US009932639B2

(12) United States Patent
Wirtz et al.

(10) Patent No.: US 9,932,639 B2
(45) Date of Patent: Apr. 3, 2018

(54) METHOD FOR PREDICTING THERAPY RESPONSIVENESS IN BASAL LIKE TUMORS

(76) Inventors: Ralph Markus Wirtz, Cologne (DE); Ralf Kronenwett, Cologne (DE)

( * ) Notice: Subject to any disclaimer, the term of this patent is extended or adjusted under 35 U.S.C. 154(b) by 786 days.

(21) Appl. No.: 12/745,668

(22) PCT Filed: Nov. 6, 2008

(86) PCT No.: PCT/EP2008/065040
§ 371 (c)(1),
(2), (4) Date: Dec. 21, 2010

(87) PCT Pub. No.: WO2009/068423
PCT Pub. Date: Jun. 4, 2009

(65) Prior Publication Data
US 2011/0118129 A1    May 19, 2011

Related U.S. Application Data
(60) Provisional application No. 60/991,391, filed on Nov. 30, 2007.

(30) Foreign Application Priority Data
Jan. 17, 2008 (EP) ..................... 08100606

(51) Int. Cl.
*C12Q 1/68* (2006.01)
(52) U.S. Cl.
CPC ...... *C12Q 1/6886* (2013.01); *C12Q 2600/112* (2013.01); *C12Q 2600/118* (2013.01); *C12Q 2600/158* (2013.01)
(58) Field of Classification Search
None
See application file for complete search history.

(56) References Cited

U.S. PATENT DOCUMENTS

| 2007/0065888 | A1* | 3/2007 | Ring | C07K 16/30 435/7.23 |
|---|---|---|---|---|
| 2007/0280948 | A1 | 12/2007 | Williams et al. | |
| 2007/0292348 | A1 | 12/2007 | Williams et al. | |
| 2008/0032293 | A1* | 2/2008 | Szabo et al. | 435/6 |

FOREIGN PATENT DOCUMENTS

| DE | 10201084 A1 | 7/2003 |
|---|---|---|
| EP | 0819696 A2 | 1/1998 |
| WO | WO-02/41992 A2 | 5/2002 |
| WO | WO-02/42759 A1 | 5/2002 |
| WO | WO-02/097413 A2 | 12/2002 |
| WO | WO-03/058649 A1 | 7/2003 |
| WO | WO-03/078662 A | 9/2003 |
| WO | WO-03 093443 A2 | 11/2003 |
| WO | WO-2006/052731 A | 5/2006 |
| WO | WO-2006/136314 A1 | 12/2006 |
| WO | WO-2007/059423 A2 | 5/2007 |
| WO | WO-2007/140410 A2 | 12/2007 |
| WO | WO-2007142987 A2 | 12/2007 |
| WO | WO-2008/089577 A1 | 7/2008 |

OTHER PUBLICATIONS

Maras et al in "Estrogen-like properties of fluorotelomer alcohols as revealed by MCF-7 breast cancer cell proliferation." (Environmental Health Perspectives 114.1: Jan. 2006: vol. 100, No. 6; entire document).*
Terasaka et al in "Using a customized DNA microarray for expression profiling of the estrogen-responsive genes to evaluate estrogen activity among natural estrogens and industrial chemicals." (Environmental Health Perspective 112.7: May 25, 2004: vol. 773, No. 9; entire document).*
Hoist et al et al ("Estrogen receptor alpha (ESR1) gene amplification is frequent in breast cancer" Nature Genetics vol. 39, No. 5, May 2007, pp. 655-660; published online Apr. 8, 2007).*
Maras et al in "Estrogen-like properties of fluorotelomer alcohols as revealed by MCF-7 breast cancer cell proliferation." (Environmental Health Perspectives 114.1: Jan. 2006: vol. 100, No. 6.*
Ihnen M et al: "Expression des ?Activated Leukocyte Cell Adhesion Molecule" (ALCAM/CD166) bei Patientinnen mit primaerem Mammakarzinom: Positive Korrelation mit dem Oestrogenrezeptorstatus and dem Auftreten von Knochenmetastasen sowie Moegliche praediktive Bedeutung bezueglich adjuvantem Therapieerfolg Senologie, [Online] vol. 4, No. 2, Jun. 2007 (Jun. 2007), XP002467762. Retrieved from the Internet: URL:http://www.thieme-connect.com/ejournals/abstract/senologie/doi/10.1055/s-2007-982961> [retrieved on Feb. 2008] abstract.
King Judy A et al: "Activated leukocyte cell adhesion molecule in breast cancer: prognostic indicator." Breast Cancer Research : BCR 2004, vol. 6, No. 5, 2004, pp. R478-R487, XP002467480. ISSN: 1465-542X abstract.
Jezierska A et al: "ALCAM/CD166 protects breast cancer cells against apoptosis and autophagy". Medical Science Monitor 2006 United States, vol. 12, No. 8, 2006, pp. BR263-BR273, XP002467763 ISSN: 1234-1010 1643-3750 abstract.

(Continued)

*Primary Examiner* — Catherine S Hibbert
(74) *Attorney, Agent, or Firm* — David G. Rosenbaum; J. Peter Paredes; Rosenbaum IP

(57) ABSTRACT

The present invention is related to a method for analyzing a clinical response of a patient suffering from or at risk of developing a neoplastic disease towards at least one given mode of treatment, said method comprising the steps of: a) obtaining a biological sample from said patient; b) determining, on a non protein basis, the expression level of three genes of interest, said genes being correlated with the Estrogen receptor (ESR) status in the sample, c) comparing the pattern of expression levels determined in (b) with one or several reference pattern(s) of expression levels; and d) predicting therapeutic success for said given mode of treatment in said patient from the outcome of the comparison in step (c); and treating based on said outcome.

4 Claims, 4 Drawing Sheets

(56) References Cited

OTHER PUBLICATIONS

Jezierska Agnieszka et al: "Activated Leukocyte Cell Adhesion Molecule (ALCAM) is associated with suppression of breast cancer cells invasion." Medical Science Monitor : International Medical Journal of Experimental and Clinical Research Jul. 2006, vol. 12, No. 7, Jul. 2006 (Jul. 2006), pp. BR245-BR256, XP002467764. ISSN: 1234-1010 figure 4.
Burkhardt M et al: "Cytoplasmic overexpression of ALCAM is prognostic of disease progression in breast cancer." Journal of Clinical Pathology APR 2006, vol. 59, No. 4, Apr. 2006 (Apr. 2006), pp. 403-409, XP002415898 ISSN: 0021-9746 figure 1; tables 2, 3.
Nagy M et al: "Optimization and validation of a fully automated silica-coated magnetic beads purification technology in forensics" Forensic Science International, Elsevier Scientific Publishers Ireland Ltd, IE, vol. 152, No. 1, Aug. 11, 2005 (Aug. 11, 2005), pp. 13-22, XP004923592 ISSN: 0379-0738 abstract.
Ihnen M et al: "Predictive impact of activated leukocyte cell adhesion molecule (ALCAM/CD166) in breast cancer" Breast Cancer Research Treatment, [Online] Jan. 2008 (Jan. 2008), XP002467790 ISSN: 0167-6806 DOI: 10.1007/s10549-007-9879-y Retrieved from the Internet: URL:http://www.springerlink.com/content/dm4787127127648p/> [retrieved on Jan. 2008] the whole document.
Fujimoto J et al: "Clinical significance of expression of estrogen receptor alpha and beta mRNAs in ovarian cancers." Oncology May 2000, vol. 58, No. 4, May 2000 (May 2000), pp. 334-341, XP002467250 ISSN: 0030-2414 abstract.
Pujol P et al: "Differential expression of estrogen receptor-alpha and -beta messenger RNAs as a potential marker of ovarian carcinogenesis." Cancer Research Dec. 1, 1998, vol. 58, No. 23, Dec. 1, 1998 (Dec. 1, 1998), pp. 5367-5373, XP002467251 ISSN: 0008-5472 abstract.
Chu Simon et al: "Estrogen receptor isoform gene expression in ovarian stromal and epithelial tumors" Journal of Clinical Endocrinology and Metabolism, Endocrine Society, Chevy Chase, MD, US, vol. 85, No. 3, Mar. 2000 (Mar. 2000), pp. 1200-1205, XP002446776 ISSN: 0021-972X abstract.
Han Li-Ping et al: "Expressions of estrogen receptor subtypes in epithelial ovarian carcinomas" Sichuan Daxue Xuebao (Yixue Ban)—Sichuan University. Journal (Medical Science Edition), Section 3, No. 17, Renmin Nanlu, Sichuan, CN, vol. 37, No. 4, Jul. 2006 (Jul. 2006), pp. 606-610, XP008082488 ISSN: 1672-173X abstract.
Kaklamani Virginia: "A genetic signature can predict prognosis and response to therapy in breast cancer: Oncotype DX." Expert Review of Molecular Diagnostics, Nov. 2006, vol. 6, No. 6, Nov. 2006 (Nov. 2006), pp. 803-809, XP009096988. ISSN: 1473-7159.
Farmer Hannah et al: "Targeting the DNA repair defect in BRCA mutant cells as a therapeutic strategy." Nature, vol. 434, No. 7035, Apr. 14, 2005 (Apr. 14, 2005), pp. 917-921, XP002516395. ISSN: 1476-4687.
Diaz Leslie K et al: "Triple negative breast carcinoma and the basal phenotype: from expression profiling to clinical practice." Advances in Anatomic Pathology Nov. 2007, vol. 14, No. 6, Nov. 2007 (Nov. 2007), pp. 419-430, XP009112644. ISSN: 1072-4109.
Cleator Susan et al: "Triple-negative breast cancer: therapeutic options" Lancet Oncology, Lancet Publishing Group, London, GB, vol. 8, No. 3, Mar. 1, 2007 (Mar. 1, 2007), pp. 235-244, XP005907670. ISSN: 1083-7159.
James Colin R et al: "BRCA1, a potential predictive biomarker in the treatment of breast cancer." The Oncologist Feb. 2007, vol. 12, No. 2, Feb. 2007 (Feb. 2007), pp. 142-150, XP002516397. ISSN: 1083-7159.
Miyazono F et al: "Quantitative c-erbB-2 but not c-erbB-1 mRNA expression is a promising marker to predict minor histopathologic response to neoadjuvant radiochemotherapy in oesophageal cancer." British Journal of Cancer, vol. 91, No. 4, Aug. 16, 2004 (Aug. 16, 2004), pp. 666-672, XP002516396. ISSN: 0007-0920.
Gong Y et al: "Determination of oestrogen-receptor status and ERBB2 status of breast carcinoma: a gene-expression profiling study" Lancet Oncology, Lancet Publishing Group, London, GB, vol. 8, No. 3, Feb. 27, 2007 (Feb. 27, 2007), pp. 203-211, XP005907666. ISSN: 1470-2045.
Teschendorff A E et al: "An immune response gene expression module identifies a good prognosis subtype in estrogen receptor negative breast cancer" Genome Biology 20070802 GB, vol. 8, No. 8, Aug. 2, 2007 (Aug. 2, 2007), XP002516399. ISSN: 1474-7596 1474-760X.
Finnegan T J et al: "Gene-expression analysis and the basal-like breast cancer subtype" Future Oncology 200702 GB, vol. 3, No. 1, Feb. 2007 (Feb. 2007), pp. 55-63, XP009112722. ISSN: 1479-6694 1744-8301.
Rakha Emad A et al: "Prognostic markers in triple-negative breast cancer" Cancer, American Cancer Society, Philadelphia, PA, US, vol. 109, No. 1, Jan. 1, 2007 (Jan. 1, 2007), pp. 25-32, XP008099489. ISSN: 0008-543X.
Ivanov Olga et al: "alpha B-crystallin is a novel predictor of resistance to neoadjuvant chemotherapy in breast cancer" Breast Cancer Research and Treatment, vol. 111, No. 3, Oct. 30, 2007 (Oct. 30, 2007), pp. 411-417. XP002516398. ISSN: 0167-6806.
Zucker S et al: "Plasma matrix metalloproteinases 7 and 9 in patients with metastatic breast cancer treated with marimastat or placebo: Eastern cooperative oncology group trial E2196" Clinical Breast Cancer 200602 US, vol. 6, No. 6, Feb. 2006 (Feb. 2006), pp. 525-529, XP009112724. ISSN: 1526-8209.
Hasmuller S et al: "Response of basal-like tumors defined by ESR1 Her-2/neu, MLPH and MMP7 to neoadjuvant chemotherapy" European Journal of Cancer, Supplement, Pergamon, Oxford, GB, vol. 6, No. 7, Apr. 18, 2008 (Apr. 18, 2008), p. 190, XP022672487. ISSN: 1359-6349.
Ring A et al: "Mechanisms of tamoxifen resistance" Endocrine-Related Cancer, vol. 11, 2004, pp. 643-658.
Sorlie T et al: "Gene expression patterns of breast carcinomas distinguish tumor subclasses with clinical implications" PNAS, vol. 98, No. 19, Sep. 11, 2001 (Sep. 11, 2001), pp. 10869-10874.
Freier K et al: "High survivin expression is associated with favorable outcome in advanced primary oral squamous cell carcinoma after radiation therapy" Int. J. Cancer, vol. 120, 2006, pp. 942-946.
Faneyte IF et al: "Breast cancer response to neoadjuvant chemotherapy: predictive markers and relation with outcome" British Journal of Cancer, vol. 88, 2003, pp. 406-412.
Jemal A et al: "Cancer statistics, 2007" CA Cancer J Clin, vol. 57, No. 1, 2007, pp. 43-66.
Veronesi U et al: "Breast cancer" Lancet, vol. 365, 2005, pp. 1727-1741.
"Cancer in Germany, 5th revised and updated edition. Society of Cancer Registries in Germany eV and the Robert Koch Institute, Saarbrücken, 2006".
van Kempen LCLT et al: "Molecular basis for the homophilic activated leukocyte cell adhesion molecule (ALCAM)-ALCAM interaction" Journal of Biological Chemistry, vol. 276, No. 28, Jul. 2007 (Jul. 13, 2001), pp. 25783-25790.
Swart GWM: "Activated leukocyte cell adhesion molecule (CD166/ALCAM): Developmental and mechanistic aspects of cell clustering and cell migration" European Journal of Cell Biology, vol. 81, Jun. 2002, pp. 313-321.
Bruder S P et al: "Mesenchymal stem cell surface antigen SB-10 corresponds to activated leukocyte cell adhesion molecule and is involved in osteogenic differentiation" vol. 13, No. 4, 1998, pp. 655-663.
Bowen MA et al: "Adhesion molecules, their receptors, and their regulations: Analysis of CD6-activated leukocyte cell adhesion molecules (ALCAM/CD166) interaction" Transplant Proc., vol. 31, 1999, pp. 795-796.
Fujiwara H et al: "Human blastocysts and endometrial epithelial cells express activated leukocyte cell adhesion molecule (ALCAM/CD166)" Journal of Clinical Endocrinology & Metabolism, vol. 88, 2003, pp. 3437-3443.
Ohneda O et al: "ALCAM (CD166): its role in hematopoietic and endothelial development", Blood, vol. 98, No. 7, Oct. 1, 2001, pp. 2134-2142.

(56) References Cited

OTHER PUBLICATIONS

King J et al: "Potential role for activated leukocyte cell adhesion molecule and neural cadherin in metastasis to the lung microcirculation" Chest, vol. 125, 2004, pp. 150S-151S.

Swart GWM et al: "Activated leukocyte cell adhesion molecule (ALCAM/CD166): Signaling at the divide of melanoma cell clustering and cell migration?" Cancer and Metastasis Reviews, vol. 24, 2005, pp. 223-236.

Kristiansen G et al: "ALCAM/CD166 is up-regulated in low-grade prostate cancer and progressively lost in high-grade lesions" Prostate, vol. 54, issue 1, Jan. 2003, pp. 34-43.

Weichert W et al: "ALCAM/CD166 is overexpressed in colorectal carcinoma and correlates with shortened patient survival" J Clin Pathol, vol. 57, 2004, pp. 1160-1164.

Verma A et al: "MEMD/ALCAM: A potential marker for tumor invasion and nodal metastasis in esophageal squamous cell carcinoma" Oncology, vol. 68, No. 4-6, 2005, pp. 462-470.

Tuck A et al: "Osteopontin expression in a group of lymph node negative breast cancer patients" Int. J. Cancer (Pred. Oncol.), vol. 79, 1998, pp. 502-508.

Rudland PS et al: "Prognostic significance of the metastasis-associated protein osteopontin in human breast cancer" Cancer Research, vol. 62, 2002, pp. 3417-3427.

Bramwell VH et al: "Serial plasma osteopontin levels have prognostic value in metastatic breast cancer" Clin Cancer Res, vol. 12 (11), Jun. 1 2006, pp. 3337-3343.

Wang-Rodriguez J et al: "Elevated osteopontin and thrombospondin expression identifies malignant human breast carcinoma but is not indicative of metastatic status" Breast Cancer Research, vol. 5, No. 5, Jul. 9, 2003, pp. R136-R143.

Das R et al: "Osteopontin induces AP-1-mediated secretion of urokinase-type plasminogen activator through c-Src-dependent epidermal growth factor receptor transactivation in breast cancer cells" Journal of Biological Chemistry, vol. 279, No. 12, 2004, pp. 11051-11064.

Shepherd FA et al: "Erlotinib in previously treated non-small-cell lung cancer" N Engl J Med, vol. 353, No. 2, Jul. 14, 2005, pp. 123-132.

\* cited by examiner

METHOD FOR PREDICTING THERAPY RESPONSIVENESS IN BASAL LIKE TUMORS

FIELD OF THE INVENTION

The present invention relates to methods for prediction of the therapeutic success of cancer therapy.

BACKGROUND OF THE INVENTION

In some neoplastic diseases, particularly gynaecological cancers like breast cancer, the response to neoadjuvant chemotherapy is comparatively low, with only about 20% of patients achieving pathological complete remission (pCR) with no tumor cells left in the breast or lymph nodes; the latter being the strongest prognostic factor for prolonged survival due to treatment benefit to date.

However, a substantial number of patients suffer severe side effects (ADRs) from highly toxic drug combinations (e.g. alopecia due to inclusion of taxanes) without additional benefit. In addition, there is a burden on national health systems due to the high cost of some therapies in this regime, especially if the chemotoxic treatments are combined with new targeted treatment options (e.g. Herceptin®, Lapatinib® and Avastin®). Moreover the new treatment options are related with some severe, probably life threatening side effects (e.g. cardiac toxicities upon combinatorial treatment with Herceptin®, gastrointestinal perforation upon combinatorial treatment with Avastin).

A better characterization of the respective tumors would thus allow a better selection of the most promising therapy in a given breast cancer patient, in order to avoid unnecessary side effects due to neoadjuvant chemotherapy in those patients which do no not draw any benefit from such therapy anyway.

Some neoplastic diseases, particularly gynaecological cancers like breast cancer (BC), are characterized the fact that approximately 80% of them are estrogen receptor positive as characterized by standard immunohistochemistry, i.e. the exhibit estrogen receptors. However, it turned out that only a fraction of these tumors are dependent on hormone ligands (i.e. estrogen) for activation of Estrogen receptors (ESR) and sustained growth of the tumor tissue.

The estrogen receptor is a member of the nuclear hormone family of intracellular receptors which is activated by the hormone 17-β-estradiol (estrogen). The main function of the estrogen receptor is that of a DNA binding transcription factor which regulates gene expression. In addition a subfraction of estrogen receptor is able to interact with receptor tyrosine kinases (e.g. Her-2/neu) on the membrane which is critical for development of resistance towards cancer therapeutics. Estrogen and the ESRs have also been implicated in breast cancer, ovarian cancer, colon cancer, prostate cancer and endometrial cancer. Advanced colon cancer is associated with a loss of ERβ (also termed ESR2), the predominant ESR in colon tissue, and colon cancer is treated with ERβ specific agonists in some cases.

As stated above, Estrogen receptors are overexpressed on the protein level in around 80% of breast cancer cases, referred to as "ESR positive". Two hypotheses have been proposed to explain why this causes tumorigenesis. One stipulates that binding of estrogen to the ESR stimulates proliferation of mammary cells, with the resulting increase in cell division and DNA replication leading to mutations. The other one states that estrogen metabolism produces genotoxic waste.

The result of both processes is disruption of cell cycle, apoptosis and DNA repair and therefore tumor formation or growth.

Different versions of the ESR1 (also termed ERα), gene have been identified (with single-nucleotide polymorphisms) and are associated with different risks of developing breast cancer.

It has turned out that, typically, ESR-positive tumors demonstrate only poor responses on neoadjuvant chemotherapy, with about 10% pathological complete remission (pCR) reported.

However, ESR-positive tumors may profit from a treatment with Tamoxifen, an estrogen-receptor antagonist used as an adjuvant hormonal treatment. Another selective estrogen receptor modulator, raloxifene, has been used as a preventative chemotherapy for women judged to have a high risk of developing breast cancer. Another anti-estrogen, ICI 182,780 (Faslodex) which acts as a complete antagonist also promotes degradation of the estrogen receptor.

Other anti estrogen drugs are Anastrozole (Arimidex®), a drug which prevents the conversion of adrenal gland androgen hormones to estrogen, Exemestane (Aromasin®) and Letrozole (Femara®), which are inhibitors for the enzyme aromatase which is involved in the production of estrogen, and Megestrol acetate (Megace®) which is a progesteron agonist acting trough competitive inhibition.

One current standard for diagnosis of early breast cancer is the determination of ESR1 by immunohistochemistry (IHC) using subsequent scoring systems. These assays are based on Protein-level measurements exhibiting limited quantitative performance and comparatively high inter- and intra-assay variabilities. Moreover, the final assessment is essentially subjective and is known to show substantial inter-operator (i.e. inter-pathologist) variance (Faneyte et al., 2003).

In this context, it has been shown that as few as 1 to 5% of ESR1 positive tumor cells within a given tumor are sufficient to specify this tumor as being potentially responsive to endocrine treatment. This is somewhat surprising as one would rather think that the 95% to 99% ESR1 protein negative tumor cells should not be dependent on estrogen and thereby not be responsive to endocrine treatment as described above. Conversely, this already shows the limitations of the protein determination of estrogen receptors as being insufficient to describe estrogen receptor dependent tumors. Clinically the 95% to 99% of estrogen receptor negative tumor cells have a high potential to be hormone dependent. Moreover, the determination of estrogen receptor status based on immunohistochemistry is highly subjective and varies between different labs (approximately 70% concordance). In view, of the marginal protein expression level of estrogen receptor being necessary to qualify for endocrine treatment this is critical.

Moreover, there are apparent differences between ESR1 positive tumors, which clearly separate the growth characteristics and dependency on solely estrogen. For example, it has been shown that a significant fraction of estrogen receptor coexpress progesteron receptor and/or the receptor tyrosine kinase Her-2/neu. This raises e.g. the possibility of estrogen independent growth capabilities via progesterone or EGFR family ligands.

Nevertheless, Estrogen receptor positive tumors do have a comparably good prognosis, while Estrogen receptor negative tumors as determined by IHC have a particularly bad prognosis.

It has yet been reported that about 20% of breast cancer cases are independent of estrogen, and are thus resistant against anti estrogen treatments (Ring et al., 2004).

These tumors, however, seem to demonstrate a better response towards chemotherapy, with about 20% pathological complete remission (pCR) reported. In addition, if Her-2/neu positive, these tumors may additionally have benefit from anti-Her-2/neu regimen such as Herceptin™ or Tykerb™. Apparently, bad prognosis tumors particularly bear the potential of benefit from combined antibody and chemotherapeutic regimen.

Still, not at least in view of the new therapeutic options, the worst prognosis among the breast cancer subgroups do have estrogen receptor negative, progesterone receptor negative and Her-2/neu receptor negative breast cancer, which are also the so called "basal like tumors" as originally defined by multiparametric gene array analysis by unsupervised cluster analysis (Sorlie et al., 2001)

However, the precise definition of the so called "basal like tumors" has been defined by fresh tissue RNA analysis using multigene arrays, and the definition of the "basal like tumors" by immunohistochemistry in fixed tissue routine samples is far from being adequate. Moreover, the "basal like tumors" itself seem to be clinically heterogenous and do contain two very different subtypes, one of which seems to have a particularly good response to chemotherapy.

A proper differentiation between these two "basal like" tumor subclasses would help to apply or develop patient or tumor specific therapies, in order to reduce side effects and improve tumor remission rates.

Moreover, new targets for newly available targeted drugs, or drugs yet to be developed, could thus be determined.

It is obvious that current methods do not suffice to characterize a high risk or low risk "basal like tumor" in a reliable and reproducible way by immunohistochemically determining it as ESR-negative, PR-negative and Her-2/neu negative.

Definitions

The term "determining the expression level of a gene/protein on a non protein basis" relates to methods which are not restricted to the secondary gene translation products, i.e proteins, but on other levels of the gene expression, like the mRNA, premRNA and genomic DNA structures.

The terms "positive receptor status" and "negative receptor status" relate to the presence or absence of a given receptor, e.g. ESR, PGR or Her-2/neu, in a tissue sample. Usually, the respective status is being determined by IHC.

The term "chemotherapy" relates to a a drug therapy which affects cell growth and cell division, i.e. which acts as a cytostatic, or which induces cell death (apoptosis). Due to their uncontrolled growth and division, cancer cells are supposed to be more affected by chemotherapy than normal cells.

The term "neoadjuvant therapy" relates to a preoperative therapy regimen consisting of a panel of hormonal, chemotherapeutic and/or antibody agents, which is aimed to shrink the primary tumour, thereby rendering local therapy (surgery or radiotherapy) less destructive or more effective, enabling breast conserving surgery and evaluation of responsiveness of tumor sensitivity towards specific agents in vivo.

The term "targeted therapy" refers to a therapy which aims at recognizing particular target molecules, which may play a role in tumor genesis or proliferation, or cell repair, for example. Such recognition may for example lead to a binding of the said target molecule, which may either enhance or decrease its activity. Drugs used for such therapy comprise, among others, antibodies, particularly monoclonal antibodies, and small molecular drugs.

Potential targets are, for example, the EGFR receptor (which plays an important role in angiogenesis), the VEGFA ligand (likewise important for angiogenesis) or PARP1 (important for cell repair, as its inhibition makes tumors characterized by oncogene defects more susceptive to chemotherapy).

The term "prediction", as used herein, relates to an individual assessment of the malignancy of a tumor, or to the expected survival rate (DFS, disease free survival; OAS, overall survival; DSS, Disease specific survival) of a patient, if the tumor is treated with a given therapy. In contrast thereto, the term "prognosis" relates to an individual assessment of the malignancy of a tumor, or to the expected survival rate (DFS, disease free survival; OAS, overall survival; DSS, Disease specific survival) of a patient, unaffected and/or independent of the tumor treatment.

The term "response marker" relates to a marker which can be used to predict the clinical response and/or clinical outcome of a patient towards a given treatment.

The term "neoplastic lesion" or "neoplastic disease" or "neoplasia" refers to a cancerous tissue this includes carcinomas, (e.g., carcinoma in situ, invasive carcinoma, metastatic carcinoma) and pre-malignant conditions, neomorphic changes independent of their histological origin (e.g. ductal, lobular, medullary, mixed origin). The term "cancer" as used herein includes carcinomas, (e.g., carcinoma in situ, invasive carcinoma, metastatic carcinoma) and pre-malignant conditions, neomorphic changes independent of their histological origin. The term "cancer" is not limited to any stage, grade, histomorphological feature, invasiveness, agressivity or malignancy of an affected tissue or cell aggregation. In particular stage 0 cancer, stage I cancer, stage II cancer, stage III cancer, stage IV cancer, grade I cancer, grade II cancer, grade III cancer, malignant cancer, primary carcinomas, and all other types of cancers, malignancies and transformations associated with the lung, ovar, cervix, endometrium, esophagus, stomach, pancreas, prostate, head and neck, renal cell, liver, colorectal or breast cancer are included. Particularly types of adenocarcinoma are included, as well as all carcinomas of unknown primary (cup-syndroms).

The terms "neoplastic lesion" or "neoplastic disease" or "neoplasia" or "cancer" are not limited to any tissue or cell type they also include primary, secondary or metastatic lesions of cancer patients, and also comprises lymph nodes affected by cancer cells or minimal residual disease cells either locally deposited (e.g. bone marrow, liver, kidney) or freely floating throughout the patients body.

The term "neoplastic cells" refer to abnormal cells that grow by cellular proliferation more rapidly than normal. As such, neoplastic cells of the invention may be cells of a benign neoplasm or may be cells of a malignant neoplasm.

Furthermore, the term "characterizing the state of a neoplastic disease" is related to, but not limited to, measurements and assessment of one or more of the following conditions: Type of tumor, histomorphological appearance, dependence on external signal (e.g. hormones, growth factors), invasiveness, motility, state by TNM (2) or similar, agressivity, malignancy, metastatic potential, and responsiveness to a given therapy.

The term "Her-2/neu" relates to a gene encoding for a cell signalling protein. Synonyms for this gene are "ErbB" or "ERBB". The three terms are being used interchangeably in this specification.

The terms "biological sample" or "clinical sample", as used herein, refer to a sample obtained from a patient. The sample may be of any biological tissue or fluid. Such samples include, but are not limited to, sputum, blood, serum, plasma, blood cells (e.g., white cells), circulating cells (e.g. stem cells or endothelial cells in the blood, tissue, core or fine needle biopsy samples, cell-containing body fluids, free floating nucleic acids, urine, stool, peritoneal fluid, and pleural fluid, liquor cerebrospinalis, tear fluid, or cells there from. Biological samples may also include sections of tissues such as frozen or fixed sections taken for histological purposes or microdissected cells or extracellular parts thereof. A biological sample to be analyzed is tissue material from a neoplastic lesion taken by aspiration or punctuation, excision or by any other surgical method leading to biopsy or resected cellular material. Such a biological sample may comprise cells obtained from a patient. The cells may be found in a cell "smear" collected, for example, by a nipple aspiration, ductal lavage, fine needle biopsy or from provoked or spontaneous nipple discharge. In another embodiment, the sample is a body fluid. Such fluids include, for example, blood fluids, serum, plasma, lymph, ascitic fluids, gynecological fluids, or urine but not limited to these fluids. The term "therapy modality", "therapy mode", "regimen" or "chemo regimen" as well as "therapy regimen" refers to a timely sequential or simultaneous administration of antitumor, and/or anti vascular, and/or anti stroma, and/or immune stimulating, and/or blood cell proliferative agents, and/or radiation therapy, and/or hyperthermia, and/or hypothermia for cancer therapy. The administration of these can be performed in an adjuvant and/or neoadjuvant mode. The composition of such "protocol" may vary in the dose of each of the single agents, timeframe of application and frequency of administration within a defined therapy window. Currently various combinations of various drugs and/or physical methods, and various schedules are under investigation.

By "array" or "matrix" an arrangement of addressable locations or "addresses" on a device is meant. The locations can be arranged in two dimensional arrays, three dimensional arrays, or other matrix formats. The number of locations can range from several to at least hundreds of thousands. Most importantly, each location represents a totally independent reaction site. Arrays include but are not limited to nucleic acid arrays, protein arrays and antibody arrays. A "nucleic acid array" refers to an array containing nucleic acid probes, such as oligonucleotides, nucleotide analogues, polynucleotides, polymers of nucleotide analogues, morpholinos or larger portions of genes. The nucleic acid and/or analogue on the array is preferably single stranded. Arrays wherein the probes are oligonucleotides are referred to as "oligonucleotide arrays" or "oligonucleotide chips." A "microarray," herein also refers to a "biochip" or "biological chip", an array of regions having a density of discrete regions of at least about 100/cm$^2$, and preferably at least about 1000/cm$^2$. The regions in a microarray have typical dimensions, e.g., diameters, in the range of between about 10-250 μm, and are separated from other regions in the array by about the same distance. A "protein array" refers to an array containing polypeptide probes or protein probes which can be in native form or denatured. An "antibody array" refers to an array containing antibodies which include but are not limited to monoclonal antibodies (e.g. from a mouse), chimeric antibodies, humanized antibodies or phage antibodies and single chain antibodies as well as fragments from antibodies.

The term "small molecule", as used herein, is meant to refer to a compound which has a molecular weight of less than about 5 kD and most preferably less than about 4 kD. Small molecules can be nucleic acids, peptides, polypeptides, peptidomimetics, carbohydrates, lipids or other organic (carbon-containing) or inorganic molecules. Many pharmaceutical companies have extensive libraries of chemical and/or biological mixtures, often fungal, bacterial, or algal extracts, which can be screened with any of the assays of the invention to identify compounds that modulate a bioactivity.

The terms "modulated" or "modulation" or "regulated" or "regulation" and "differentially regulated" as used herein refer to both upregulation [i.e., activation or stimulation, e.g., by agonizing or potentiating] and down regulation [i.e., inhibition or suppression, e.g., by antagonizing, decreasing or inhibiting].

The term "transcriptome" relates to the set of all messenger RNA (mRNA) molecules, or "transcripts", produced in one or a population of cells. Importantly, this term includes also non-translated RNAs such as "micro RNA's", which affect cellular characteristics because of gene regulation functions (silencing or activation or stabilization or degradation of other genes and transcripts). The term can be applied to the total set of transcripts in a given organism, or to the specific subset of transcripts present in a particular cell type. Unlike the genome, which is roughly fixed for a given cell line (excluding mutations), the transcriptome can vary with external environmental conditions. Because it includes all RNA transcripts in the cell, the transcriptome reflects the genes that are being actively expressed at any given time, with the exception of mRNA degradation phenomena such as transcriptional attenuation. It also includes posttranscriptional events such as alternative splicing. The discipline of transcriptomics examines the expression level of mRNAs in a given cell population, often using high-throughput techniques based on DNA microarray technology.

The term "expression levels" refers, e.g., to a determined level of gene expression. The term "pattern of expression levels" refers to a determined level of gene expression compared either to a reference gene (e.g. housekeeper or inversely regulated genes) or to a computed average expression value (e.g. in DNA-chip analyses). A pattern is not limited to the comparison of two genes but is more related to multiple comparisons of genes to reference genes or samples. A certain "pattern of expression levels" may also result and be determined by comparison and measurement of several genes disclosed hereafter and display the relative abundance of these transcripts to each other.

Alternatively, a differentially expressed gene disclosed herein may be used in methods for identifying reagents and compounds and uses of these reagents and compounds for the treatment of cancer as well as methods of treatment. The differential regulation of the gene is not limited to a specific cancer cell type or clone, but rather displays the interplay of cancer cells, muscle cells, stromal cells, connective tissue cells, other epithelial cells, endothelial cells of blood vessels as well as cells of the immune system (e.g. lymphocytes, macrophages, killer cells).

A "reference pattern of expression levels", within the meaning of the invention shall be understood as being any pattern of expression levels that can be used for the comparison to another pattern of expression levels. In a preferred embodiment of the invention, a reference pattern of expression levels is, e.g., an average pattern of expression levels observed in a group of healthy or diseased individuals, serving as a reference group.

"Primer pairs" and "probes", within the meaning of the invention, shall have the ordinary meaning of this term which is well known to the person skilled in the art of molecular biology. In a preferred embodiment of the invention "primer pairs" and "probes", shall be understood as being polynucleotide molecules having a sequence identical, complementary, homologous, or homologous to the complement of regions of a target polynucleotide which is to be detected or quantified. In yet another embodiment nucleotide analogues and/or morpholinos are also comprised for usage as primers and/or probes.

"Individually labeled probes", within the meaning of the invention, shall be understood as being molecular probes comprising a polynucleotide, oligonucleotide or nucleotide analogue and a label, helpful in the detection or quantification of the probe. Preferred labels are fluorescent molecules, luminescent molecules, radioactive molecules, enzymatic molecules and/or quenching molecules.

"Arrayed probes", within the meaning of the invention, shall be understood as being a collection of immobilized probes, preferably in an orderly arrangement. In a preferred embodiment of the invention, the individual "arrayed probes" can be identified by their respective position on the solid support, e.g., on a "chip".

The phrase "tumor response", "therapeutic success", or "response to therapy" refers, in the adjuvant chemotherapeutic setting to the observation of a defined tumor free or recurrence free survival time (e.g. 2 years, 4 years, 5 years, 10 years). This time period of disease free survival may vary among the different tumor entities but is sufficiently longer than the average time period in which most of the recurrences appear. In a neo-adjuvant therapy modality, response may be monitored by measurement of tumor shrinkage and regression due to apoptosis and necrosis of the tumor mass.

The term "recurrence" or "recurrent disease" includes distant metastasis that can appear even many years after the initial diagnosis and therapy of a tumor, or local events such as infiltration of tumor cells into regional lymph nodes, or occurrence of tumor cells at the same site and organ of origin within an appropriate time.

"Prediction of recurrence" or "prediction of therapeutic success" does refer to the methods described in this invention. Wherein a tumor specimen is analyzed for it's gene expression and furthermore classified based on correlation of the expression pattern to known ones from reference samples. This classification may either result in the statement that such given tumor will develop recurrence and therefore is considered as a "non responding" tumor to the given therapy, or may result in a classification as a tumor with a prolonged disease free post therapy time.

"Biological activity" or "bioactivity" or "activity" or "biological function", which are used interchangeably, herein mean an effector or antigenic function that is directly or indirectly exerted by a polypeptide (whether in its native or denatured conformation), or by any fragment thereof in vivo or in vitro. Biological activities include but are not limited to binding to polypeptides, binding to other proteins or molecules, enzymatic activity, signal transduction, activity as a DNA binding protein, as a transcription regulator, ability to bind damaged DNA, etc. A bioactivity can be modulated by directly affecting the subject polypeptide. Alternatively, a bioactivity can be altered by modulating the level of the polypeptide, such as by modulating expression of the corresponding gene.

The term "marker" or "biomarker" refers to a biological molecule, e.g., a nucleic acid, peptide, protein, hormone, etc., whose presence or concentration can be detected and correlated with a known condition, such as a disease state.

The term "ligand", as used herein, relates to a molecule that is able to bind to and form a complex with a biomolecule to serve a biological purpose. In a narrower sense, it is an effector molecule binding to a site on a target protein, by intermolecular forces such as ionic bonds, hydrogen bonds and Van der Waals forces. The docking (association) is usually reversible (dissociation). Actual irreversible covalent binding between a ligand and its target molecule is rare in biological systems. Ligand binding to receptors often alters the chemical conformation, i.e. the three dimensional shape of the receptor protein. The conformational state of a receptor protein determines the functional state of a receptor. The tendency or strength of binding is called affinity. Ligands include substrates, inhibitors, activators, and neurotransmitters.

The term "agonist", as used herein, relates to a substance that binds to a specific receptor and triggers a response in the cell. It mimics the action of an endogenous ligand that binds to the same receptor.

The term "receptor", as used herein, relates to a protein on the cell membrane or within the cytoplasm or cell nucleus that binds to a specific molecule (a ligand), such as a neurotransmitter, hormone, or other substance, and initiates the cellular response to the ligand. Ligand-induced changes in the behavior of receptor proteins result in physiological changes that constitute the biological actions of the ligands.

The term "signalling pathway" is related to any intra- or intercellular process by which cells converts one kind of signal or stimulus into another, most often involving ordered sequences of biochemical reactions out- and inside the cell, that are carried out by enzymes and linked through hormones and growth factors (intercellular), as well as second messengers (intracellular), the latter resulting in what is thought of as a "second messenger pathway". In many signalling pathways, the number of proteins and other molecules participating in these events increases as the process emanates from the initial stimulus, resulting in a "signal cascade" and often results in a relatively small stimulus eliciting a large response.

The term "marker gene," as used herein, refers to a differentially expressed gene whose expression pattern may be utilized as part of a predictive, prognostic or diagnostic process in healthy conditions, premalignant disease status, malignant neoplasia or cancer evaluation, or which, alternatively, may be used in methods for identifying compounds useful for the treatment or prevention of malignant neoplasia and head and neck, colon or breast cancer in particular. A marker gene may also have the characteristics of a target gene.

"Target gene", as used herein, refers to a differentially expressed gene involved in cancer or pre-cancerous lesions, e.g., lung, head and neck, colon, ovarian or breast cancer in a manner in which modulation of the level of the target gene expression or of the target gene product activity may act to ameliorate symptoms of malignant neoplasia and lung, liver, endometrium, ovarian, cervix, esophagus, stomach, pancreas, prostate, head and neck, renal cell, colorectal or breast cancer in particular. A target gene may also have the characteristics of a marker gene.

The term "expression level", as used herein, relates to each step within the process by which a gene's DNA sequence is converted into functional protein (i.e. ligands) via RNA intermediates and particularly to the amount of said conversion.

The term "hybridization based method", as used herein, refers to methods imparting a process of combining complementary, single-stranded nucleic acids or nucleotide analogues into a single double stranded molecule. Nucleotides or nucleotide analogues will bind to their complement under normal conditions, so two perfectly complementary strands will bind to each other readily. In bioanalytics, very often labeled, single stranded probes are in order to find complementary target sequences. If such sequences exist in the sample, the probes will hybridize to said sequences which can then be detected due to the label. Other hybridization based methods comprise microarray and/or biochip methods. Therein, probes are immobilized on a solid phase, which is then exposed to a sample. If complementary nucleic acids exist in the sample, these will hybridize to the probes and can thus be detected. These approaches are also known as "array based methods". Yet another hybridization based method is PCR, which is described below. When it comes to the determination of expression levels, hybridization based methods may for example be used to determine the amount of mRNA for a given gene.

"Serial analysis of gene expression" (SAGE) is a method for comprehensive analysis of gene expression patterns, which is based on the facts that (i) a short sequence tag (10-14 bp) contains sufficient information to uniquely identify a transcript provided that that the tag is obtained from a unique position within each transcript; (ii) sequence tags can be linked together to from long serial molecules that can be cloned and sequenced; and (iii) quantitation of the number of times a particular tag is observed provides the expression.

The term "a PCR based method" as used herein refers to methods comprising a polymerase chain reaction (PCR). This is a method of exponentially amplifying nucleic acids, e.g. DNA by enzymatic replication in vitro. As PCR is an in vitro technique, it can be performed without restrictions on the form of DNA, and it can be extensively modified to perform a wide array of genetic manipulations. When it comes to the determination of expression levels, a PCR based method may for example be used to detect the presence of a given mRNA by (1) reverse transcription of the complete mRNA pool (the so called transcriptome) into cDNA with help of a reverse transcriptase enzyme, and (2) detecting the presence of a given cDNA with help of respective primers. This approach is commonly known as reverse transcriptase PCR (rtPCR).

Moreover, PCR-based methods comprise e.g. real time PCR, and, particularly suited for the analysis of expression levels, kinetic or quantitative PCR (qPCR).

The term "Quantitative real-time PCR" (qPCR)" refers to any type of a PCR method which allows the quantification of the template in a sample. Quantitative real-time PCR comprise different techniques of performance or product detection as for example the TaqMan technique or the LightCycler technique. The TaqMan technique, for examples, uses a dual-labelled fluorogenic probe. The TaqMan real-time PCR measures accumulation of a product via the fluorophore during the exponential stages of the PCR, rather than at the end point as in conventional PCR. The exponential increase of the product is used to determine the threshold cycle, CT, i.e. the number of PCR cycles at which a significant exponential increase in fluorescence is detected, and which is directly correlated with the number of copies of DNA template present in the reaction. The set up of the reaction is very similar to a conventional PCR, but is carried out in a real-time thermal cycler that allows measurement of fluorescent molecules in the PCR tubes. Different from regular PCR, in TaqMan real-time PCR a probe is added to the reaction, i.e., a single-stranded oligonucleotide complementary to a segment of 20-60 nucleotides within the DNA template and located between the two primers. A fluorescent reporter or fluorophore (e.g., 6-carboxyfluorescein, acronym: FAM, or tetrachlorofluorescin, acronym: TET) and quencher (e.g., tetramethylrhodamine, acronym: TAMRA, of dihydrocyclopyrroloindole tripeptide "minor groove binder", acronym: MGB) are covalently attached to the 5' and 3' ends of the probe, respectively [2]. The close proximity between fluorophore and quencher attached to the probe inhibits fluorescence from the fluorophore. During PCR, as DNA synthesis commences, the 5' to 3' exonuclease activity of the Taq polymerase degrades that proportion of the probe that has annealed to the template (Hence its name: Taq polymerase+PacMan). Degradation of the probe releases the fluorophore from it and breaks the close proximity to the quencher, thus relieving the quenching effect and allowing fluorescence of the fluorophore. Hence, fluorescence detected in the real-time PCR thermal cycler is directly proportional to the fluorophore released and the amount of DNA template present in the PCR.

The term "planar waveguide" (PWG) relates to detection chips and chambers for performing multiplex PCR assays, as for example disclosed in WO2007059423, which has been filed by the applicant of the present invention and which is incorporated herein by reference. Such planar waveguides may be used in methods of performing a multiplex polymerase chain reaction (PCR) assay with a single fluorogenic dye. Compared to other biochips or microarrays they have a far better sensitivity and do thus put aside the need of an additional amplification step.

The term "determining the protein level", as used herein, refers to methods which allow the quantitative and/or qualitative determination of one or more proteins in a sample. These methods include, among others, protein purification, including ultracentrifugation, precipitation and chromatography, as well as protein analysis and determination, including the use protein microarrays, two-hybrid screening, blotting methods including western blot, one- and two dimensional gelelectrophoresis, isoelectric focusing as well as methods being based mass spectrometry like MALDI-TOF and the like.

The term "method based on the electrochemical detection of molecules" relates to methods which make use of an electrode system to which molecules, particularly biomolecules like proteins, nucleic acids, antigens, antibodies and the like, bind under creation of a detectable signal. Such methods are for example disclosed in WO0242759, WO0241992 and WO02097413 filed by the applicant of the present invention, the content of which is incorporated by reference herein. These detectors comprise a substrate with a planar surface which is formed, for example, by the crystallographic surface of a silicon chip, and electrical detectors which may adopt, for example, the shape of interdigital electrodes or a two dimensional electrode array. These electrodes carry probe molecules, e.g. nucleic acid probes, capable of binding specifically to target molecules, e.g. target nucleic acid molecules. The probe molecules are for example immobilized by a Thiol-Gold-binding. For this purpose, the probe is modified at its 5'- or 3'-end with a thiol group which binds to the electrode comprising a gold surface. These target nucleic acid molecules may carry, for example, an enzyme label, like horseradish peroxidise (HRP) or alkaline phosphatase. After the target molecules have bound to the probes, a substrate is then added (e.g., α-naphthyl phosphate or 3,3'5,5'-tetramethylbenzidine which is converted by said enzyme, particularly in a redox-reaction. The product of said reaction, or a current generated in said reaction due to an exchange of electrons, can then be detected with help of the electrical detector in a site specific manner.

The term "anamnesis" relates to patient data gained by a physician or other healthcare professional by asking specific questions, either of the patient or of other people who know the person and can give suitable information (in this case, it is sometimes called heteroanamnesis), with the aim of obtaining information useful in formulating a diagnosis and providing medical care to the patient. This kind of information is called the symptoms, in contrast with clinical signs, which are ascertained by direct examination.

The term "etiopathology" relates to the course of a disease, that is its duration, its clinical symptoms, and its outcome.

The term "detection of a ligand and/or receptor" as used herein means both the qualitative detection of the presence of the respective gene as well as the quantitative detect detection of the expression level of the respective gene, e.g. by quantitative reverse transcriptase PCR.

The term "nucleic acid molecule" is intended to indicate any single- or double stranded nucleic acid molecule comprising DNA (cDNA and/or genomic DNA), RNA (preferably mRNA), PNA, LNA and/or Morpholino.

The term "stringent conditions" relates to conditions under which a probe will preferably hybridize to its target subsequence and much less to other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion (or other salts) at pH 7.0 to 8.3 and the temperature is at least about 30° C. for short probes (e.g. 10 to 50 nucleotides) and at least about 60° C. for longer probes. Stringent conditions may also be achieved with the addition of destabilizing agents, such as formamide and the like.

The term "fragment of the nucleic acid molecule" is intended to indicate a nucleic acid comprising a subset of a nucleic acid molecule according to one of the claimed sequences. The same is applicable to the term "fraction of the nucleic acid molecule".

The term "variant of the nucleic acid molecule" refers herein to a nucleic acid molecule which is substantially similar in structure and biological activity to a nucleic acid molecule according to one of the claimed sequences.

The term "homologue of the nucleic acid molecule" refers to a nucleic acid molecule the sequence of which has one or more nucleotides added, deleted, substituted or otherwise chemically modified in comparison to a nucleic acid molecule according to one of the claimed sequences, provided always that the homologue retains substantially the same binding properties as the latter.

The term "derivative", as used herein, refers to a nucleic acid molecule that has similar binding characteristics to a target nucleic acid sequence as a nucleic acid molecule according to one of the claimed sequences.

The term "sequence identity of at least X %" refers to a sequence identity as determined after a sequence alignment carried out with the family of BLAST algorithms as accessible on the respective Internet domain provided by NCBI.

Object of the Invention

It is one object of the present invention to detect cancer subtypes which are characterized in that they are estrogen receptor negative, progesterone receptor negative and Her-2/neu receptor negative ("basal type tumors"), in order to provide chemotherapeutic and/or antibody based regimen specially suitable for these cancer types.

It is another object of the present invention to provide means to further differentiate between different basal type tumor subgroups.

It is another object of the present invention to identify basal type tumors having high probability to respond to chemotherapy regimen ("low risk basal type tumors"), and/or to identify basal type tumors that do not respond to chemotherapy ("high risk basal type tumors") in order to identify target genes that might serve as more effective treatment alternatives.

It is another object of the present invention to offer a more robust and specific diagnostic assay system than conventional immunohistochemistry for clinical routine fixed tissue samples that better helps the physician to select individualized treatment modalities. In a more preferred embodiment the disclosed method can be used to select chemotherapeutic and/or antibody based regimen for breast cancers exhibiting reduced estrogen receptor expression on RNA and or/protein level.

It is another object of the present invention to detect new targets for newly available targeted drugs, or to determine drugs yet to be developed.

SUMMARY OF THE INVENTION

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

According to the invention, a method is provided for predicting a clinical response of a patient suffering from or at risk of developing a neoplastic disease towards at least one given mode of treatment, said method comprising the steps of:
  a) obtaining a biological sample from said patient;
  b) determining, on a non-protein basis, the expression level of at least one gene of interest, said gene being correlated with the Estrogen receptor (ESR) status in the said sample,
  c) comparing the pattern of expression levels determined in (b) with one or several reference pattern(s) of expression levels; and
  d) predicting therapeutic success for said given mode of treatment in said patient from the outcome of the comparison in step (c).

Figure 1:
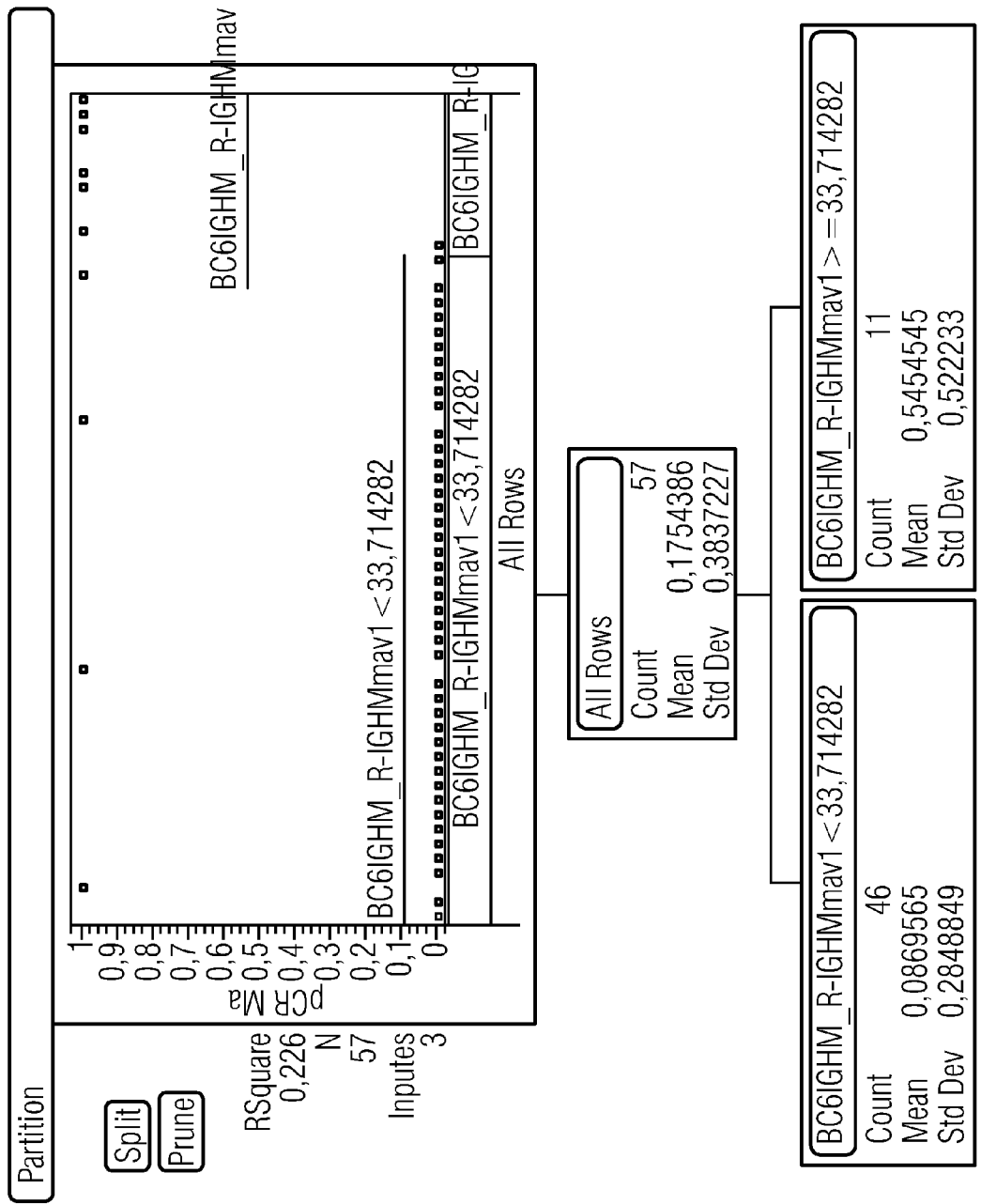
FIG. 1 shows results of an Affymetrix array analysis (HG U133A) in fresh tissue biopsies or RT-kPCR analysis in fixed tissue biopsies of high risk breast tumors.

Basically, a deviating expression level of either of the aforementioned genes can have different reasons, these being
- gene amplification of an oncogene (frequently seen in Her-2/neu)
- overexpression of the respective gene due to an altered Methylation pattern, mutations
- altered properties of a transcription factor, a promotor or another factor which leads to an upregulation of the expression level of the said agent.

In a preferred embodiment of the present invention, it is provided that the at least one gene of interest is correlated with a negative Estrogen receptor status.

The applicants have, in various studies, analyzed breast tumors with ESR1 negative and Her-2/neu negative status as determined with Immunochistochemistry (IHC) and/or Fluorescence In situ Hybridization (FISH). Core needle biopsy specimen of these tumors were analyzed on the DNA and RNA level by quantitative PCR, RT-PCR and array technologies.

During this process, the applicants have, surprisingly, identified a number of candidate genes which are correlated with, and are thus predictive for, subgroups of Estrogen receptor negative tumors (ESR−).

The following genes were identified to be useful for the discrimination of ESR1 positive tumors (IHC status 4, i.e. ESR status as determined with Immunohistochemistry) from ESR1 negative tumors (IHC status 0) by having high expression levels, high variance and fold change levels as identified in fresh tumor tissue.

TABLE 1 genes that can be used to discriminate ESR1 positive tumors from ESR1 negative tumors

| Gene Symbol | MapLocation | LocusLink | OMIM | UniGene | RefSeq Transcript |
|---|---|---|---|---|---|
| AKR7A3 | chr1p35.1-p36.23 | 22977 | 608477 | Hs.6980 | NM_012067 |
| ALCAM | chr3q13.1 | 214 | 601662 | Hs.150693 | NM_001627 |
| AR | chrXq11.2-q12 | 367 | 313700 | Hs.496240 | NM_000044, NM_001011645 |
| ASPN | chr9q22 | 54829 | 608135 | Hs.435655 | NM_017680 |
| BCL2 | chr18q21.33\|18q21.3 | 596 | 151430 | Hs.150749 | NM_000633, NM_000657 |
| C6orf211 | chr6q25.1 | 79624 | | Hs.15929 | NM_024573 |
| CA12 | chr15q22 | 771 | 603263 | Hs.210995 | NM_001218, NM_206925 |
| CCND1 | chr11q13 | 595 | 168461 | Hs.523852 | NM_053056 |
| CDC2 | chr10q21.1 | 983 | 116940 | Hs.334562 | NM_001786, NM_033379 |
| CEACAM6 | chr19q13.2 | 4680 | 163980 | Hs.466814 | NM_002483 |
| CELSR1 | chr22q13.3 | 9620 | 604523 | Hs.252387 | NM_014246 |
| CHI3L1 | chr1q32.1 | 1116 | 601525 | Hs.382202 | NM_001276 |
| COL4A5 | chrXq22 | 1287 | 303630 | Hs.369089 | NM_000495, NM_033380, NM_033381 |
| CPE | chr4q32.3 | 1363 | 114855 | Hs.75360 | NM_001873 |
| CRAT | chr9q34.1 | 1384 | 600184 | Hs.12068 | NM_000755, NM_004003, NM_144782 |
| CXCL9 | chr4q21 | | 601704 | Hs.77367 | |
| CX3CR1 | chr3p21\|3p21.3 | 1524 | 601470 | Hs.78913 | NM_001337 |
| CXCL10 | chr4q21 | 3627 | 147310 | Hs.413924 | NM_001565 |
| DNAJC12 | chr10q22.1 | 56521 | 606060 | Hs.260720 | NM_021800, NM_201262 |
| ERBB2/ Her-2/neu | chr17q11.2-q12\|17q21.1 | | | | |
| ERBB4 | chr2q33.3-q34 | 2066 | 600543 | Hs.390729 | NM_005235 |
| ESR1 | chr6q25.1 | 2099 | 133430 | Hs.208124 | NM_000125 |
| FBP1 | chr9q22.3 | 2203 | 229700 | Hs.494496 | NM_000507 |
| FLJ20152 | chr5p15.1 | 54463 | | Hs.481704 | NM_019000 |
| FOS | chr14q24.3 | 2353 | 164810 | Hs.25647 | NM_005252 |
| FOXA1 | chr14q12-q13 | 3169 | 602294 | Hs.163484 | NM_004496 |
| GATA3 | chr10p15 | 2625 | 131320 | Hs.524134 | NM_001002295, NM_002051 |
| IGF2 | chr11p15.5 | 3481 | 147470 | Hs.523414 | NM_001007139 |
| ITPR1 | chr3p26-p25 | 3708 | 147265 | Hs.374613 | NM_002222 |
| JMJD2B | chr19p13.3 | 23030 | | Hs.371013 | NM_015015 |
| KIAA0303 | chr5q12.3 | 23227 | | Hs.133539 | XM_291141 |
| KIAA0882 | chr4q31.21 | 23158 | | Hs.480819 | NM_015130 |
| KIF5C | chr2q23.1 | 3800 | 604593 | Hs.435557 | XM_377774 |
| KRT23 | chr17q21.2 | 25984 | 606194 | Hs.9029 | NM_015515, NM_173213 |

TABLE 1-continued genes that can be used to discriminate ESR1 positive tumors from ESR1 negative tumors

| Gene Symbol | MapLocation | LocusLink | OMIM | UniGene | RefSeq Transcript |
|---|---|---|---|---|---|
| KRT5 | chr12q12-q13 | 3852 | 148040 | Hs.433845 | NM_000424 |
| KRT6B | chr12q12-q13 | 3854 | 148042 | Hs.524438 | NM_005555 |
| MAPT | chr17q21.1 | 4137 | 157140 | Hs.101174 | NM_005910, NM_016834, NM_016835, NM_016841 |
| MLPH | chr2q37.3 | 79083 | 606526 | Hs.102406 | NM_024101 |
| MMP7 | chr11q21-q22 | 4316 | 178990 | Hs.2256 | NM_002423 |
| NAT1 | chr8p23.1-p21.3 | 9 | 108345 | Hs.155956 | NM_000662 |
| PHGDH | chr1p12 | 26227 | 606879 | Hs.487296 | NM_006623 |
| PROM1 | chr4p15.32 | 8842 | 604365 | Hs.479220 | NM_006017 |
| RARRES1 | chr3q25.32 | 5918 | 605090 | Hs.131269 | NM_002888, NM_206963 |
| RRM2 | chr2p25-p24 | 6241 | 180390 | Hs.226390 | NM_001034 |
| RRM2 | chr2p25-p24 | 6241 | 180390 | Hs.226390 | NM_001034 |
| S100A8 | chr1q21 | 6279 | 123885 | Hs.416073 | NM_002964 |
| SCNN1A | chr12p13 | 6337 | 600228 | Hs.130989 | NM_001038 |
| SCUBE2 | chr11p15.3 | 57758 | | Hs.523468 | NM_020974 |
| SEMA3C | chr7q21-q31 | 10512 | 602645 | Hs.269109 | NM_006379 |
| SFRP1 | chr8p12-p11.1 | 6422 | 604156 | Hs.213424 | NM_003012 |
| SLC7A5 | chr16q24.3 | 8140 | 600182 | Hs.513797 | NM_003486 |
| SLC7A8 | chr14q11.2 | 23428 | 604235 | Hs.22891 | NM_012244, NM_182728 |
| SLPI | chr20q12 | 6590 | 107285 | Hs.517070 | NM_003064 |
| SOCS2 | chr12q | 8835 | 605117 | Hs.485572 | NM_003877 |
| SOD2 | chr6q25.3 | 6648 | 147460 | Hs.487046 | NM_000636 |
| SPDEF | chr6p21.3 | 25803 | 608144 | Hs.485158 | NM_012391 |
| STC2 | chr5q35.1 | 8614 | 603665 | Hs.233160 | NM_003714 |
| TFF1 | chr21q22.3 | 7031 | 113710 | Hs.162807 | NM_003225 |
| TFF3 | chr21q22.3 | 7033 | 600633 | Hs.82961 | NM_003226 |
| TOP2A | chr17q21-q22 | 7153 | 126430 | Hs.156346 | NM_001067 |
| TPX2 | chr20q11.2 | 22974 | 605917 | Hs.244580 | NM_012112 |
| TRIM29 | chr11q22-q23 | 23650 | | Hs.504115 | NM_012101, NM_058193 |
| TSPAN-1 | chr1p34.1 | 10103 | | Hs.38972 | NM_005727 |
| VAV3 | chr1p13.3 | 10451 | 605541 | Hs.267659 | NM_006113 |

The terms "MapLocation, LocusLink, Unigene and OMIM" relate to databases in which the respective proteins are listed under the given access number. These databases can be accessed over the NCBI server.

Out of these, preferred genes are the following:

TABLE 2 preferred genes that can be used to discriminate ESR1 positive tumors from ESR1 negative tumors

| Gene Symbol | MapLocation | LocusLink | OMIM | UniGene | RefSeq Transcript |
|---|---|---|---|---|---|
| ALCAM | chr3q13.1 | 214 | 601662 | Hs.150693 | NM_001627 |
| ASPN | chr9q22 | 54829 | 608135 | Hs.435655 | NM_017680 |
| BCL2 | chr18q21.33\|18q21.3 | 596 | 151430 | Hs.150749 | NM_000633, NM_000657 |
| CCND1 | chr11q13 | 595 | 168461 | Hs.523852 | NM_053056 |
| CDC2 | chr10q21.1 | 983 | 116940 | Hs.334562 | NM_001786, NM_033379 |
| CEACAM6 | chr19q13.2 | 4680 | 163980 | Hs.466814 | NM_002483 |
| CELSR1 | chr22q13.3 | 9620 | 604523 | Hs.252387 | NM_014246 |
| CHI3L1 | chr1q32.1 | 1116 | 601525 | Hs.382202 | NM_001276 |
| COL4A5 | chrXq22 | 1287 | 303630 | Hs.369089 | NM_000495, NM_033380, NM_033381 |

TABLE 2-continued preferred genes that can be used to discriminate
ESR1 positive tumors from ESR1 negative tumors

| Gene Symbol | MapLocation | LocusLink | OMIM | UniGene | RefSeq Transcript |
|---|---|---|---|---|---|
| CPE | chr4q32.3 | 1363 | 114855 | Hs.75360 | NM_001873 |
| CRAT | chr9q34.1 | 1384 | 600184 | Hs.12068 | NM_000755, NM_004003, NM_144782 |
| CXCL9 | | | | | |
| CXCL10 | chr4q21 | 3627 | 147310 | Hs.413924 | NM_001565 |
| DNAJC12 | chr10q22.1 | 56521 | 606060 | Hs.260720 | NM_021800, NM_201262 |
| FLJ20152 | chr5p15.1 | 54463 | | Hs.481704 | NM_019000 |
| FOS | chr14q24.3 | 2353 | 164810 | Hs.25647 | NM_005252 |
| ITPR1 | chr3p26-p25 | 3708 | 147265 | Hs.374613 | NM_002222 |
| JMJD2B | chr19p13.3 | 23030 | | Hs.371013 | NM_015015 |
| KIF5C | chr2q23.1 | 3800 | 604593 | Hs.435557 | XM_377774 |
| KRT23 | chr17q21.2 | 25984 | 606194 | Hs.9029 | NM_015515, NM_173213 |
| KRT5 | chr12q12-q13 | 3852 | 148040 | Hs.433845 | NM_000424 |
| KRT6B | chr12q12-q13 | 3854 | 148042 | Hs.524438 | NM_005555 |
| LOC492304 | chr11p15.5 | 3481 | 147470 | Hs.523414 | NM_001007139 |
| MAPT | chr17q21.1 | 4137 | 157140 | Hs.101174 | NM_005910, NM_016834, NM_016835, NM_016841 |
| MAST4 | chr5q12.3 | 23227 | | Hs.133539 | XM_291141 |
| MLPH | chr2q37.3 | 79083 | 606526 | Hs.102406 | NM_024101 |
| MMP7 | chr11q21-q22 | 4316 | 178990 | Hs.2256 | NM_002423 |
| PHGDH | chr1p12 | 26227 | 606879 | Hs.487296 | NM_006623 |
| PROM1 | chr4p15.32 | 8842 | 604365 | Hs.479220 | NM_006017 |
| RARRES1 | chr3q25.32 | 5918 | 605090 | Hs.131269 | NM_002888, NM_206963 |
| S100A8 | chr1q21 | 6279 | 123885 | Hs.416073 | NM_002964 |
| SCUBE2 | chr11p15.3 | 57758 | | Hs.523468 | NM_020974 |
| SLC7A5 | chr16q24.3 | 8140 | 600182 | Hs.513797 | NM_003486 |
| SLPI | chr20q12 | 6590 | 107285 | Hs.517070 | NM_003064 |
| SOCS2 | chr12q | 8835 | 605117 | Hs.485572 | NM_003877 |
| SOD2 | chr6q25.3 | 6648 | 147460 | Hs.487046 | NM_000636 |
| STC2 | chr5q35.1 | 8614 | 603665 | Hs.233160 | NM_003714 |
| TFF1 | chr21q22.3 | 7031 | 113710 | Hs.162807 | NM_003225 |
| TOP2A | chr17q21-q22 | 7153 | 126430 | Hs.156346 | NM_001067 |
| TRIM29 | chr11q22-q23 | 23650 | | Hs.504115 | NM_012101, NM_058193 |
| TSPAN1 | chr1p34.1 | 10103 | | Hs.38972 | NM_005727 |

The applicants have analysed these genes and were able to assign the said genes to given biological motifs which are correlated with, and are thus predictive for, subgroups of Estrogen receptor (ESR) negative tumors. By way of illustration and not by limitation these motifs may be selected from the group comprising at least
 extracellular matrix degradation (Table 3),
 growth factor signaling (Table 4),
 immune cell infiltration (Table 5) and/or
 basal markers (Table 6).

Extracellular Matrix degradation is frequently caused by Matrix Metalloproteinases. For this reason, most preferred genes are part of the Matrix Metalloproteinase gene family, and the Keratin gene family, which both tend to exhibit bimodal distribution of expression values. Such genes are, for example
 Matrix Metallo Proteinases (MMP), particularly MMP1, MMP3, MMP7, MMP9, MMP11 and MMP12, most preferred MMP7

TABLE 3

Preferred genes related genes related to extracellular matrix degradation

| Gene Symbol | MapLocation | LocusLink | OMIM | UniGene | RefSeq Transcript |
|---|---|---|---|---|---|
| MMP1 | chr11q22.3 | | 120353 | Hs.83169 | |
| MMP3 | chr 11q22.3 | | 185250 | Hs.375129 | |
| MMP7 | chr 11q21-q22 | | 178990 | Hs.2256 | |
| MMP9 | chr 20q11.2-q13.1 | | 120361 | Hs.297413 | |
| MMP11 | chr 22q11.2-q11.23 | | 185261 | Hs.143751 | |
| MMP12 | chr 11q22.3 | | 601046 | Hs.1695 Hs.645661 | |

Genes related to growth factor signalling may for example encode for hormone receptors, growth factor receptors, growth factor ligands, inhibitors and the like. Such genes comprise, for example, genes encoding a receptor from the ErbB-family, or a gene correlated with the Progesteron receptor (PGR) status in the said sample.

TABLE 4

Preferred genes related related to growth factor signalling

| Gene Symbol | MapLocation | Entrez | LocusLink | OMIM | UniGene | RefSeq Transcript |
|---|---|---|---|---|---|---|
| PGR | chr11q22-q23 | | | 607311 | Hs.368072 | |
| ESR | chr6q25.1 | | | 133430 | Hs.208124 | |
| EGFR/ErbB1 | chr7p12 | | | 131550 | Hs.488293 | |
| VEGFR | chr4q11-q12 | | | 191306 | Hs.479756 | |
| ErbB2/Her-2/neu | chr17q11.2-q12; 17q21.1 | | | 164870 | Hs.446352 | |
| ErbB4 | chr2q33.3-q34 | | | 600543 | Hs.390729 | |
| C-Kit | chr 4q11-q12 | | | 164920 | Hs.479754 | |
| PDGFRA | chr 4q11-q13 | | | 173490 | Hs.74615 | |
| PDGFRB | chr 5q31-q32 | | | 173410 | Hs.509067 | |
| PDGFRC | chr 4q32 | | | 608452 | Hs.570855 | |
| C-MET | chr 7q31 | | | 164860 | Hs.132966 | |

Genes related to immune cell infiltration may be selected from the following table (listing is not exclusive):

TABLE 5

Preferred genes related to immune cell infiltration

| Gene Symbol | MapLocation | Entrez | Locus Link | OMIM | UniGene | RefSeq |
|---|---|---|---|---|---|---|
| CD79A | chr19q13.2 | NM_001783 | 973 | 112205 | Hs.79630 | NM_001783, NM_021601 |
| CD79B | chr17q23 | NM_000626 | 974 | 147245 | Hs.89575 | NM_000626, NM_021602 |
| CD83 | chr6p23 | NM_004233 | 9308 | 604534 | Hs.484703 | NM_004233 |
| IGBP1 | chrXq13.1-q13.3 | NM_001551 | 3476 | 300139 | Hs.496267 | NM_001551 |
| IGH@ | chr14q32.33 | S65761 | 3492 | | Hs.510635 | |
| IGH@, IGHG1 | chr14q32.33 | U80164 | | | | |
| IGH@, IGHG1, IGHG2, IGHM | chr14q32.33 | M87789 | 3502 | | 147120 Hs.525646 | |
| IGH@, IGHG1, IGHG2, IGHM, LOC390714, MGC27165 | chr14q32.33, chr16p11.2 | BG340548 | 283650 | | Hs.366 | —, XM_372632 |
| IGHA2, MGC27165 | chr14q32.33 | S55735 | 283650 | | Hs.366 | |
| IGHD | chr14q32.33 | AI858004 | 3495 | | 147170 Hs.439852 | |
| IGHD | chr14q32.33 | AJ275469 | | | Hs.525874 | |
| IGHD | chr14q32.33 | BG340670 | | | Hs.448957 | |
| IGHD | chr14q32.33 | AW134608 | 3495 | | 147170 Hs.439852 | |
| IGHD, IGHG1, IGHM, MGC27165 | chr14q32.33 | M21388 | | | Hs.112610 | |
| IGHG1 | chr14q32.33 | M24668 | | | Hs.531234 | |
| IGHG1 | chr14q32.33 | L23519 | | | Hs.449011 | |
| IGHG1 | chr14q32.33 | L14454 | 3507 | | 147020 Hs.525647 | |
| IGHG1 | chr14q32.33 | L14455 | | | Hs.497707 | |
| IGHG1 | chr14q32.33 | L14456 | | | Hs.497707 | |
| IGHG1 | chr14q32.33 | AJ225092 | | | | |
| IGHG1 | chr14q32.33 | X58397 | | | Hs.532509 | |
| IGHG1 | chr14q32.33 | AJ275397 | | | | |
| IGHG1 | chr14q32.33 | U92706 | | | | |
| IGHG1 | chr14q32.33 | S74639 | | | Hs.497707 | |
| IGHG1, IGHG3 | chr14q32.33 | AJ275408 | | | | |
| IGHG1, IGHM | chr14q32.33 | U80139 | | | | |
| IGHG1, IGHM, MGC27165 | chr14q32.33 | AJ239383 | 283650 | | Hs.366 | |

TABLE 5-continued

Preferred genes related to immune cell infiltration

| Gene Symbol | MapLocation | Entrez | Locus Link | OMIM | UniGene | RefSeq |
|---|---|---|---|---|---|---|
| IGHG1, LOC390714 | chr14q32.33, chr16p11.2 | M87268 | | | Hs.448957 | —, XM_372632 |
| IGHG1, LOC390714 | chr14q32.33, chr16p11.2 | AB035175 | | | | —, XM_372632 |
| IGHM | chr14q32.33 | BC001872 | 3495 | 147170 | Hs.439852 | |
| IGHM | chr14q32.33 | M24669 | 3495 | 147170 | Hs.439852 | |
| IGHM | chr14q32.33 | L23518 | 3495 | 147170 | Hs.439852 | |
| IGHM | chr14q32.33 | X17115 | 3495 | 147170 | Hs.439852 | |
| IGHM | chr14q32.33 | BF002659 | 3495 | 147170 | Hs.439852 | |
| IGHMBP2 | chr11q13.2-q13.4 | L14754 | 3508 | 600502 | Hs.503048 | NM_002180 |
| IGHMBP2 | chr11q13.2-q13.4 | AF052128 | 3508 | 600502 | Hs.503048 | NM_002180 |
| IGJ | chr4q21 | AV733266 | 3512 | 147790 | Hs.381568 | NM_144646 |
| IGKC | chr2p12 | X72475 | | | Hs.512130 | |
| IGKC | chr2p12 | BC005332 | 3514 | 147200 | Hs.449621 | |
| IGKC | chr2p12 | M63438 | 3514 | 147200 | Hs.449621 | |
| IGKV1D-13 | chr2p12 | AW408194 | 28902 | | Hs.390427 | |
| IGL@ | chr22q11.1-q11.2 | X93006 | | | Hs.449598 | |
| IGL@, IGLC2 | chr22q11.1-q11.2, chr22q11.2 | X57812 | 28831, 3535, 3538 | | Hs.449585 | |
| IGL@, IGLC2 | chr22q11.1-q11.2, chr22q11.2 | AA680302 | 3546 | 147240 | Hs.449587 | |
| IGL@, IGLC2 | chr22q11.1-q11.2, chr22q11.2 | AV698647 | | | Hs.458262 | |
| IGLC2 | chr22q11.2 | M87790 | | | Hs.458262 | |
| IGLC2 | chr22q11.2 | H53689 | | | Hs.449582 | |
| IGLC2 | chr22q11.2 | AF043586 | 28831, 3535, 3538 | | Hs.449585 | |
| IGLC2 | chr22q11.2 | D87021 | 96610 | | Hs.449601 | |
| IGLC2 | chr22q11.2 | AJ249377 | 28831 | | Hs.517455 | |
| IGLC2, IGLJ3 | chr22q11.1-q11.2, chr22q11.2 | AF047245 | | | Hs.537013 | |
| IGLC2, IGLJ3 | chr22q11.1-q11.2, chr22q11.2 | AF234254 | 28831 | | Hs.517453 | |
| IGLJ3 | chr22q11.1-q11.2 | AB001733 | 28831 | | Hs.517453 | |
| IGLJ3 | chr22q11.1-q11.2 | AB014341 | 28831 | | Hs.517453 | |
| IGLL1 | chr22q11.23 | NM_020070 | 3543 | 146770 | Hs.348935 | NM_020070, NM_152855 |
| IGLL1, LOC91316 | chr22q11.23 | AL022324 | 3543 | 146770 | Hs.348935 | NM_020070, NM_152855, XM_498877 |
| IGLV6-57 | chr22q11.2 | AI952772 | 3546 | 147240 | Hs.449587 | |
| IGSF1 | chrXq25 | NM_001555 | 3547 | 300137 | Hs.22111 | NM_001555, NM_205833 |
| IGSF2 | chr1p13 | NM_004258 | 9398 | 604516 | Hs.74115 | NM_004258 |
| IGSF3 | chr1p13 | AB007935 | 3321 | 603491 | Hs.171057 | NM_001007237, NM_001542 |
| IGSF4 | chr11q23.2 | NM_014333 | 23705 | 605686 | Hs.370510 | NM_014333 |
| IGSF4 | chr11q23.2 | AL519710 | 23705 | 605686 | Hs.370510 | NM_014333 |
| IGSF4 | chr11q23.2 | AF132811 | 23705 | 605686 | Hs.370510 | NM_014333 |
| IGSF4B | chr1q21.2-q22 | AF062733 | 57863 | | Hs.365689 | NM_021189 |
| IGSF4B | chr1q21.2-q22 | AI564838 | 57863 | | Hs.365689 | NM_021189 |
| IGSF4B | chr1q21.2-q22 | AL050219 | 57863 | | Hs.365689 | NM_021189 |
| IGSF4B | chr1q21.2-q22 | AL050219 | 57863 | | Hs.365689 | NM_021189 |
| IGSF4B | chr1q21.2-q22 | AI951798, AU129642 | 57863 | | Hs.365689 | NM_021189 |
| IGSF4C | chr19q13.31 | AC005525 | 199731 | | Hs.370984 | NM_145296 |
| IGSF4C | chr19q13.31 | AC005525 | 199731 | | Hs.370984 | NM_145296 |
| IGSF4C | chr19q13.31 | AW204383 | 199731 | | Hs.370984 | NM_145296 |
| IGSF6 | chr16p12-p13 | NM_005849 | 10261 | 606222 | Hs.530902 | NM_005849 |
| ILT10 | chr19q13.4 | NM_024317 | 79166 | | Hs.202680 | NM_024317 |
| ILT7 | chr19q13.4 | AF041261 | 23547 | 607517 | Hs.406708 | NM_012276 |
| ISLR | chr15q23-q24 | NM_005545 | 3671 | 602059 | Hs.513022 | NM_005545, NM_201526 |
| KIR2DL1 | chr19q13.4 | U24078 | 3802 | 604936 | Hs.512572 | NM_014218 |
| KIR2DL2 | chr19q13.4 | L76669 | 3812 | 604947 | Hs.380156 | NM_014219 |
| KIR2DL3 | chr19q13.4 | AF022048 | 3804 | 604938 | Hs.512573 | NM_014511, NM_015868 |
| KIR2DL4 | chr19q13.4 | NM_002255 | 3805 | 604945 | Hs.166085 | NM_002255 |
| KIR2DL4 | chr19q13.4 | AF276292 | 3805 | 604945 | Hs.166085 | NM_002255 |
| KIR2DL4 | chr19q13.4 | AF002256 | 3805 | 604945 | Hs.166085 | NM_002255 |
| KIR2DL5 | chr19p13.3 | AF217487 | 115653, 3811 | | Hs.278457 | NM_020535 |
| KIR2DL5, KIR3DL2, KIR3DL3 | chr19p13.3, chr19q13.4, chr19q13.42 | AJ000190 | 115653, 3811 | | Hs.278457 | NM_006737, NM_020535, NM_153443 |
| KIR2DS1 | chr19q13.4 | NM_014512 | 3805 | 604945 | Hs.166085 | NM_014512 |
| KIR2DS2 | chr19q13.4 | L76668 | 3812 | 604947 | Hs.380156 | NM_012312 |
| KIR2DS3 | chr19q13.4 | NM_012313 | 3812 | 604947 | Hs.380156 | NM_012313 |

TABLE 5-continued

Preferred genes related to immune cell infiltration

| Gene Symbol | MapLocation | Entrez | Locus Link | OMIM | UniGene | RefSeq |
|---|---|---|---|---|---|---|
| KIR2DS4 | chr19q13.4 | AF135564 | 3806 | 604952 | Hs.512574 | NM_012314, NM_178228 |
| KIR2DS5 | chr19q13.4 | NM_014513 | 3812 | 604947 | Hs.380156 | NM_014513 |
| KIR3DL1 | chr19q13.4 | AF262973 | 3812 | 604947 | Hs.380156 | NM_013289 |
| KIR3DL2 | chr19q13.4 | L76666 | 3812 | 604947 | Hs.380156 | NM_006737 |
| KIR3DL2 | chr19q13.4 | NM_006737 | 3812 | 604947 | Hs.380156 | NM_006737 |
| KIR3DL2 | chr19q13.4 | AF263617 | 3812 | 604947 | Hs.380156 | NM_006737 |
| KIR3DL2 | chr19q13.4 | X93596 | 3812 | 604947 | Hs.380156 | NM_006737 |
| KIR3DL3 | chr19q13.42 | AC006293 | 3804 | 604938 | Hs.512573 | NM_153443 |
| LILRA1 | chr19q13.4 | NM_006863 | 10859, 11024 | | Hs.534393 | NM_006863 |
| LILRA1 | chr19q13.4 | AF025529 | 10859, 11024 | | Hs.534393 | NM_006863 |
| LILRA2 | chr19q13.4 | NM_006866 | 11027 | 604812 | Hs.534394 | NM_006866 |
| LILRA2 | chr19q13.4 | U82278 | 11027 | 604812 | Hs.534394 | NM_006866 |
| LILRA2 | chr19q13.4 | U82276 | 11027 | 604812 | Hs.534394 | NM_006866 |
| LILRA2 | chr19q13.4 | U82277 | 11027 | 604812 | Hs.534394 | NM_006866 |
| LILRA3 | chr19q13.4 | NM_006865 | 11026 | 604818 | Hs.113277 | NM_006865 |
| LILRB1 | chr19q13.4 | NM_006669 | 10859 | 604811 | Hs.149924 | NM_006669 |
| LILRB1 | chr19q13.4 | AF009007 | 10859 | 604811 | Hs.149924 | NM_006669 |
| LILRB2 | chr19q13.4 | NM_005874 | 10990 | 604814 | Hs.306230 | NM_005874 |
| LILRB2, LILRB6 | chr19q13.4 | AF004231 | 10990 | 604814 | Hs.306230 | NM_005874, NM_024318 |
| LILRB3 | chr19q13.4 | AF009635 | 10288, 11025, 79168 | | Hs.515601 | NM_006864 |
| LILRB3 | chr19q13.4 | AF009634 | 10288, 11025, 79168 | | Hs.515601 | NM_006864 |
| LILRB3 | chr19q13.4 | AF009643 | 10288, 11025, 79168 | | Hs.515601 | NM_006864 |
| LILRB3 | chr19q13.4 | AF009644 | 10288, 11025, 79168 | | Hs.515601 | NM_006864 |
| LILRB4 | chr19q13.4 | U82979 | 11006 | 604821 | Hs.67846 | NM_006847 |
| LILRB5 | chr19q13.4 | NM_006840 | 10990 | 604814 | Hs.306230 | NM_006840 |
| LILRB6 | chr19q13.4 | NM_024318 | 10288, 11025, 79168 | | Hs.515601 | NM_024318 |
| LOC440361 | chr16p11.2 | AJ275383 | | | | XM_496145 |
| LOC91316 | chr22q11.23 | AA398569 | 91316 | | Hs.407693 | XM_498877 |
| LOC91316 | chr22q11.23 | AU158566 | 91316 | | Hs.407693 | XM_498877 |
| LOC91316 | chr22q11.23 | AK025313 | | | | XM_498877 |
| LOC91316 | chr22q11.23 | L02326 | | | | XM_498877 |
| LRIG1 | chr3p14 | AB050468 | 26018 | 608868 | Hs.518055 | NM_015541 |
| LRIG2 | chr1p13.1 | NM_014813 | 9860 | 608869 | Hs.448972 | NM_014813 |
| PIGR | chr1q31-q41 | NM_002644 | 5284 | 173880 | Hs.497589 | NM_002644 |
| SEMA3A | chr7p12.1 | NM_006080 | 10371 | 603961 | Hs.252451 | NM_006080 |
| SEMA3B | chr3p21.3 | NM_004636 | 7869 | 601281 | Hs.82222 | NM_001005914, NM_004636 |
| SEMA3C | chr7q21-q31 | AI962897 | 10512 | 602645 | Hs.269109 | NM_006379 |
| SEMA3C | chr7q21-q31 | NM_006379 | 10512 | 602645 | Hs.269109 | NM_006379 |
| SEMA3D | chr7q21.11 | AA343027 | 223117 | | Hs.201340 | NM_152754 |
| SEMA3D | chr7q21.11 | AU145680 | 223117 | | Hs.201340 | NM_152754 |
| SEMA3F | chr3p21.3 | U38276 | 6405 | 601124 | Hs.32981 | NM_004186 |
| SEMA3F | chr3p21.3 | NM_004186 | 6405 | 601124 | Hs.32981 | NM_004186 |
| SEMA3F | chr3p21.3 | U38276 | 6405 | 601124 | Hs.32981 | NM_004186 |
| SEMA4A | chr1q22 | NM_022367 | 64218 | 607292 | Hs.408846 | NM_022367 |
| SEMA4C | chr2q11.2 | AI949392 | 54910 | 604462 | Hs.516220 | NM_017789 |
| SEMA4C | chr2q11.2 | NM_017789 | 54910 | 604462 | Hs.516220 | NM_017789 |
| SEMA4D | chr9q22-q31 | NM_006378 | 10507 | 601866 | Hs.511748 | NM_006378 |
| SEMA4F | chr2p13.1 | NM_004263 | 10505 | 603706 | Hs.25887 | NM_004263 |
| SEMA4F | chr2p13.1 | AL136552 | 10505 | 603706 | Hs.25887 | NM_004263 |
| SEMA4G | chr10q24.32 | NM_017893 | 57715 | | Hs.444359 | NM_017893 |
| SEMA7A | chr15q22.3-q23 | AF071542 | 8482 | 607961 | Hs.24640 | NM_003612 |
| TCF3 | chr19p13.3 | AA768906, M31523 | 6929 | 147141 | Hs.371282 | NM_003200 |
| TCF3 | chr19p13.3 | AI655986, M31523 | 6929 | 147141 | Hs.371282 | NM_003200 |
| TCF3 | chr19p13.3 | M31523 | 6929 | 147141 | Hs.371282 | NM_003200 |
| TCF3 | chr19p13.3 | M31222 | 6929 | 147141 | Hs.371282 | NM_003200 |
| TCF3 | chr19p13.3 | BE962186 | 6929 | 147141 | Hs.371282 | NM_003200 |
| TCF3 | chr19p13.3 | AW062341, BG393795 | 6929 | 147141 | Hs.371282 | NM_003200 |
| TCF3 | chr19p13.3 | X52078 | 6929 | 147141 | Hs.371282 | NM_003200 |
| TCF3 | chr19p13.3 | AL117663 | 6929 | 147141 | Hs.371282 | NM_003200 |
| TIE1 | chr1p34-p33 | NM_005424 | 7075 | 600222 | Hs.78824 | NM_005424 |
| TTID | chr5q31 | NM_006790 | 9499 | 604103 | Hs.84665 | NM_006790 |
| VSIG4 | chrXq12-q13.3 | NM_007268 | 11326 | 300353 | Hs.8904 | NM_007268 |
| CXCL9 | | | | | | |
| CXCL10 | chr4q21 | | | 147310 | Hs.413924 | NM_001565 |
| IGHM | chr14q32.33 | | | 147020 | Hs.510635 | |
| MMP9 | chr20q11.2-q13.1 | | | 120361 | Hs.297413 | |

Genes related to basal markers (the term "basal markers" is derived from the appearance of the respective cells, which is similar to basal cells) may be selected from the following table (listing is not exclusive):

TABLE 6

Preferred genes related to basal markers

| Gene Symbol | MapLocation | LocusLink | OMIM | UniGene | RefSeq Transcript |
|---|---|---|---|---|---|
| KRT5 | chr12q12-q13 | | 148040 | Hs.694210 | |
| | | | | Hs.694210 | |
| KRT6A | chr12q12-q13 | | 148041 | Hs.433845 | |
| KRT6B | chr12q12-q13 | | 148042 | Hs.433845 | |
| KRT14 | chr17q12-q21 | | 148066 | Hs.654380 | |
| KRT23 | chr17q21.2 | | 606194 | Hs.9029 | |
| KRT17 | chr17q12-q21 | | 148069 | Hs.2785 | |
| MLPH | chr2q37.3 | 79083 | 606526 | Hs.102406 | NM_024101 |

Out of these, most preferred genes are the following:

TABLE 7a

Preferred genes in the context of the present invention

| Gene Symbol | Biological motif |
|---|---|
| ERBB2/Her-2/neu | growth factor signallling |
| MMP7 | extracellular matrix degradation |
| MMP1 | extracellular matrix degradation |
| PGR | growth factor signallling |
| ESR1 | growth factor signallling |
| MLPH | extracellular matrix degradation/ basal marker |
| IGHM | immune cell infiltration |
| C-Kit | growth factor signalling |
| C-MET | growth factor signalling |
| EGFR | growth factor signalling |

Out of these, MMP7, MLPH, ESR1 and Her-2/neu are subject of a most preferred embodiment of the invention.

Furthermore, it is preferred that at least one mode of treatment for which prediction is sought is a neaoadjuvant chemotherapy and/or targeted therapy. These two types of therapy are particularly promising in ESR negative (ESR−) tumors which are not susceptible to endocrine treatment with, for example, tamoxifen.

The terms "neoadjuvant therapy", "chemotherapy" and "targeted therapy" have been defined above.

Said chemotherapy may comprise the administration of at least one agent selected from the group consisting of Cyclophosphamid (Endoxan®, Cyclostin®). Adriamycin (Doxorubicin) (Adriblastin®), BCNU (Carmustin) (Carmubris®), Busulfan (Myleran®), Bleomycin (Bleomycin®), Carboplatin (Carboplat®), Chlorambucil (Leukeran®), Cis-Platin (Cisplatin®), Platinex (Platiblastin®), Dacarbazin (DTIC®; Detimedac®), Docetaxel (Taxotere®), Epirubicin (Farmorubicin®), Etoposid (Vepesid®), 5-Fluorouracil (Fluroblastin®, Fluorouracil®), Gemcitabin (Gemzar®), Ifosfamid (Holoxan®), Interferon alpha (Roferon®), Irinotecan (CPT 11, Campto®), Melphalan (Alkeran®), Methotrexat (Methotrexat®, Farmitrexat®), Mitomycin C (Mitomycin®), Mitoxantron (Novantron®), Oxaliplatin (Eloxatine®), Paclitaxel (Taxol®), Prednimustin (Sterecyt®), Procarbazin (Natulan®), Pemetrexed (Alimta®), Ralitrexed (Tomudex®), Topotecan (Hycantin®), Trofosfamid (Ixoten®), Vinblastin (Velbe®), Vincristin (Vincristin®), Vindesin (Eldisine®) and/or Vinorelbin (Navelbine®).

In particularly preferred embodiments, the following agents and equitoxic modifications thereof are used alone or in combination:

Taxanes (e.g. Docetaxel, Paclitaxel)
Anthracyclins (e.g. Doxorubicine, Epirubicine, Daunorubicin, Mitoxanthrone, Idarubicin or modifications thereof as e.g. pegylated anthracycline)
Cyclophosphamide
Tubulin modifying agents (e.g. vinorelbine)
5'FU based regimen (including Capecitabine)
Antibody based regimen (e.g. Avastin®, Erbitux®, Herceptin®)
Small molecule inhibitors (e.g. Tykerb®, Tarceva®, Iressa®, Sutent®, Nexavar®)

Recent studies by the inventors showed furthermore that an overexpression of MMP7 and/or MLPH is frequently correlated with irregularities in the expression of the breast cancer gene BRCA1. BRCA1 (breast cancer 1, early onset) belongs to a class of genes known as tumor suppressors, which maintain genomic integrity to prevent uncontrolled proliferation. The multifactorial BRCA1 protein product is involved in DNA damage repair, ubiquitination, transcriptional regulation as well as other functions. Genetic variations leading to a BRCA1 deficiency have been implicated in a number of hereditary cancers, namely breast, ovarian and prostate, as an important DNA repair system is lost which otherwise would prevent the accumulation of mutations fostering tumor genesis.

Genetic variations of BRCA1 comprise, for example, (i) an altered methylation pattern, (ii) a mutation in the gene (i.e. SNP or gene rearrangements), or (iii) an alteration of the respective promoter.

BRCA1 deficient tumors are known to be quickly growing tumors which are comparatively resistant against chemotherapy. A novel treatment for these tumors are inhibitors of Poly (ADP-ribose) polymerase 1 (PARP1). PARP1 plays a role in repair of single-stranded DNA (ssDNA) breaks. In the absence of PARP1, when these breaks are encountered during DNA replication, the replication fork stalls and double-strand DNA (dsDNA) breaks accumulate. These dsDNA breaks are repaired via homologous recombination (HR) repair. If the HR pathway is functioning, PARP1 deficient mutants do not show an unhealthy phenotype. However, BRCA1 is necessary for the HR pathway to work properly. Therefore, cells which are deficient in BRCA1 are highly sensitive to PARP1 inhibition or knock-down, resulting in cell death by apoptosis, in stark contrast to cells with at least one functionally intact copy of BRCA1.

This means that BRCA1 deficient mutants are likely to become prone to apoptosis in case they are also deficient for PARP1, or PARP1 is inhibited by a respective drug, i.e. a PARP1 inhibitor (see above); preferably if the latter is combined with chemotherapy, e.g. taxane administration. This means, in turn, that PARP1 inhibition therapy is a promising treatment for BRCA1 deficient tumors.

Current tests for BRCA1 deficiencies, as for example performed within clinical trials to test the efficacy of KU-0059436 (PARP1 inhibitor manufactured by Astra Zeneca), comprise only those deficiencies caused by mutation of the BRCA1 gene (i.e. variant (ii)), as these tests perform sequence analysis or use sequence specific probes. BRCA1 deficiencies due to altered methylation patterns, or an alteration of the respective promoter, are not detected by these tests.

Furthermore, direct determination of the expression level of BRCA1 is complex, as the median expression level of BRCA1 is downregulated by approximately 2 fold, which is in the range of assay variabilities for some gene expression determination methods (e.g. RT-PCR), and is highly dependent on the share of tumor cells in the respective sample.

In contrast thereto, the inventors found that simultaneous detection of MMP7 and/or MLPH reveals as well the latter variants discussed above (i.e. variant (i) and (iii), and will thus help to provide adequate treatment for those patients which have a BRCA1 deficiency that is not caused by mutation of the BRCA1 gene itself. The inventors estimate that, by the said simultaneous detection of MMP7 and/or MLPH, between 2 to 5 times more BRCA1 deficient tumors can be detected than with the current tests, which means that up to 5 times more patients can be provided with adequate PARP1 inhibition treatment.

Interestingly, the said correlation between irregularities in BRCA1 expression and the gene expression level of other genes is not only valid for MMP7 and MLPH, but also for MMP1, ESR1, PGR, Her-2/neu, IGHM, C-Kit, C-MET and EGFR, and other genes identified in this application.

Moreover, the inventors have demonstrated that MMP7 positive tumors were frequently found to have decreased expression of RB1 (Retinoblastoma 1), i.e. there seems to be a correlation between MMP7 overexpression and RB1 deficiency. RB1 is not only a negative regulator of the cell cycle (indeed, it has been the first tumor suppressor gene identified), but also involved in the stabilization of constitutive chromatin.

Again, RB1 deficient tumors are particularly sensitive towards intensified chemotherapy and also inclusion of PARP1 inhibitors, namely for the same reasons as mentioned in the context of BRCA1. This means that, for example, PARP1 inhibition and addition of taxanes is beneficial in these tumors, which otherwise have a poor outcome.

As for BRCA1, direct determination of the expression level of RB1 is complex, as the median expression level of RB1 is downregulated by approximately 2 fold, which is in the range of assay variabilities for some gene expression determination methods (e.g. RT-PCR), and is highly dependent on the share of tumor cells in the respective sample.

Again, it is thus beneficial to measure the gene expression of a gene correlated with RB1 irregularities. Interestingly, the said correlation between irregularities in RB1 expression and the gene expression level of other genes is not only valid for MMP7 and MLPH, but also for MMP1, ESR1, PGR, Her-2/neu, IGHM, C-Kit, C-MET and EGFR, and other genes identified in this application.

The above phenomena apply as well to the CCND1 gene (Cyclin D1 (PRAD1). The CCND1 protein contributes to the progression of the cell cycle in the G1/S checkpoint. CCND1 overexpression (for instance as a consequence of CCND1 amplification) might result in loss of control over genetic damage at this point and in an accumulation of chromosomal aberrations.

The inventors found, during their studies related to this invention, that the detection of RB1, BRCA1 and/or CCND1 irregularities and/or deficiencies in basal type tumors, as identified by e.g. MMP7 and/or MLPH expression levels, renders such tumors particularly sensitive to defined therapeutic interventions. The said genes are listed in the following table:

In a preferred embodiment, it is thus provided that the mode of treatment for which prediction is sought is a therapy directed to the inhibition of homologous recombination repair. This is, for example, being done be determination of MMP7 and/or MLPH, which are reciprocally correlated with RB1, BRCA1 and CCND1. This means that a high expression level of MMP7 and/or MLPH is an indication for a therapy directed to the inhibition of homologous recombination repair. Examples for such therapy are Inhibitors of Poly (ADP-ribose) polymerase 1 (PARP1), like AZD2281 (KU-0059436), FR247304, AG14361, GPI 15427, GPI 16539, caffeine metabolites like 1,7-dimethylxanthine, 3-methylxanthine 1-methylxanthine, theobromine and theophylline, and others.

In yet another preferred embodiment of the present invention, it is provided that the method further comprises the steps of
    e) determining the expression level of at least one gene correlated and/or coexpressed with a receptor from the ErbB-family in the said sample, and/or
    f) determining the expression level of at least one gene correlated and/or coexpressed with the Progesteron receptor (PGR) status in the said sample.

In this regard we have found that the expression of Her-2/neu is quite often negatively correlated with EGFR expression. EGFR expression is particularly prominent in tumors exhibiting low expression of Her-2/neu, ESR1 and PGR. However, the exact and robust determination of EGFR expression is critical both on protein and mRNA level. It is particularly difficult to determine a clear cut threshold to reliably discriminate between high and low expressing breast tumors, in part because of a narrow dynamic range of EGFR expression and technical variations due to assay platform or variable tissue composition in independent tumor samples of the same tumor.

In contrast, the determination of MMP7, as an example, is robust and more reliable, as the dynamic range is broader and the data distribution is almost bimodal, enabling to define a biologically and clinically meaningful threshold between high and low expressing tumors.

Moreover, we have found that high expression of MMP7 excludes high expression of Her-2/neu, ESR1 and PGR (="basal like tumors"). Still not all, but about 50% of the basal like tumors express MMP7. Most preferred is the combination of MMP7 with MLPH, which trends to exhibit bimodal distribution of expression values, while being strongly associated with ESR1 expression.

There is evidence for a correlation between ESR and growth factor receptor pathways, such as the ErbB pathway. The ESR can be phosphorylated at the serine-118 position within AF-1 by the MAPKs ERK1 and ERK2, which are downstream components of the Her-2/neu signalling pathway, the latter being a member of the ErbB receptor family.

TABLE 7b

| Gene Symbol | MapLocation | LocusLink | OMIM | UniGene | RefSeq Transcript | Negatively correleated/ coexpressed with |
|---|---|---|---|---|---|---|
| RB1 | 13q14.2 | | 180200 | Hs.408528 | | MMP7/MLPH |
| BRCA1 | 17q21 | | 113705 | Hs.194143 | | MMP7/MLPH |
| CCND1 | 11q13 | | 168461 | Hs.523852 | | MMP7/MLPH |

Genes related to growth factor signalling may for example encode for growth factor receptors, growth factor ligands, inhibitors and the like.

Genes which meet the above criteria, i.e. that they are correlated and/or coexpressed with a receptor from the ErbB-family or correlated and/or coexpressed with the Progesteron receptor (PGR) status in the said sample are listed in the following table:

TABLE 8a

Genes correlated and/or coexpressed with a receptor from the ErbB-family

| Gene symbol | MapLocation | LocusLink | Genbank ID | Unigene_v133_ID | Correleated/ coexpressed with |
|---|---|---|---|---|---|
| LASP1 | | 3927 | NM_006148.1 | 75080 | ErbB |
| CACNB1 | | 782 | NM_000723.1 | 635 | ErbB |
| RPL19RPL19 | | 6143 | NM_000981.1 | 252723 | ErbB |
| PPARGBP | | 5469 | Y13467 | 15589 | ErbB |
| CrkRS | | | NM_016507.1 | 123073 | ErbB |
| NEUROD2 | | 4761 | AB021742.1 | 322431 | ErbB |
| MLN64 | | 10948 | NM_006804.1 | 77628 | ErbB |
| TELETHONIN | | 8557 | NM_003673.1 | 111110 | ErbB |
| PNMT | | 5409 | NM_002686.1 | 1892 | ErbB |
| ERBB2 | | 2064 | X03363.1 | 323910 | ErbB |
| GRB7 | | 2886 | AB008790.1 | 86859 | ErbB |
| PSMD3 | | 5709 | NM_002809.1 | 9736 | ErbB |
| GCSFG | | 1440 | NM_000759.1 | 2233 | ErbB |
| KIAA0130 | | 9862 | AI023317 | 23106 | ErbB |
| c-erbA-1 | | | X55005 | 7067 | ErbB |
| NR1D1 | | 9572 | X72631 | 211606 | ErbB |
| MLN51 | | 22794 | NM_007359.1 | 83422 | ErbB |
| CDC6 | | 990 | U77949.1 | 69563 | ErbB |
| RARA | | | U41742.1 | 5914 | ErbB |
| TOP2A | | 7153 | NM_001067.1 | 156346 | ErbB |
| IGFBP4 | | | NM_001552.1 | 1516 | ErbB |
| CCR7 EBI1 | | CCR7 | NM_001838.1 | 1652 | ErbB |
| SMARCE1 | | 6605 | NM_003079.1 | 332848 | ErbB |
| KRT10 | | 3858 | X14487 | 99936 | ErbB |
| KRT12 | | | NM_000223.1 | 66739 | ErbB |
| hHKa3-II | | 3884 | NM_002279.2 | 32950 | ErbB |
| MLLT6 | | 4302 | NM_005937 | 349196 | ErbB |
| ZNF144 | | 7703 | XM_008147 | 184669 | ErbB |
| PIP5K2B | | 8396 | NM_138687 | 432736 | ErbB |
| TEM7 | | 57125 | NM_020405 | 125036 | ErbB |
| ZNFN1A3 | | 22806 | XM_012694 | 258579 | ErbB |
| WIRE | | 147179 | XM_085731 | 13996 | ErbB |
| PSMB3 | | 5691 | NM_002795 | 82793 | ErbB |
| MGC9753 Variant a | | 93210 | NM_033419 | 91668 | ErbB |
| MGC9753 Variant c | | | | | ErbB |
| MGC9753 Variant d | | | | | ErbB |
| MGC9753 Variant e | | | | | ErbB |
| MGC9753 Variant g | | | | | ErbB |
| MGC9753 Variant h | | | | | ErbB |
| MGC9753 Variant i | | | | | ErbB |
| ORMDL3 | | 94103 | AF395708 | 374824 | ErbB |
| MGC15482 | | 84961 | NM_032875 | 194498 | ErbB |
| PPP1R1B | | 84152 | NM_032192 | 286192 | ErbB |
| MGC14832 | | 84299 | NM_032339 | 333526 | ErbB |
| LOC51242 | | 51242 | NM_057555 | 12101 | ErbB |
| FLJ20291 | | 54883 | NM_017748 | 8928 | ErbB |
| Pro2521 | | 55876 | NM_018530 | 19054 | ErbB |
| Link-GEFII | | 51195 | NM_016339 | 118562 | ErbB |
| CTEN | | 84951 | NM_032865 | 294022 | |

TABLE 8b

Genes correlated and/or coexpressed with the Progesteron receptor (PGR)

| Gene Symbol | MapLocation | LocusLink | OMIM | UniGene | RefSeq Transcript | Correleated/ coexpressed with |
|---|---|---|---|---|---|---|
| MAPT | chr17q21.1 | 4137 | 157140 | Hs.101174 | NM_005910, NM_016834, NM_016835, NM_016841 | PGR |
| MLPH | chr2q37.3 | 79083 | 606526 | Hs.102406 | NM_024101 | PGR |

As part of this invention, it was found that tumors demonstrating elevated expression levels of MMP7 and low and/or undetectable MLPH levels belong to the group of "basal-like tumors" exhibiting low expression of ESR1 and Her-2/neu, but yet having a high risk if not treated by chemotherapy regimen.

Particularly preferred at least one of the receptors the expression level of which is determined is Her-2/neu.

Her-2/neu (also known as ErbB-2, ERBB2) is a member of the ErbB protein family, more commonly known as the epidermal growth factor receptor family. Her-2/neu is notable for its role in the pathogenesis of breast cancer and as a target of treatment. It is a cell membrane surface-bound receptor tyrosine kinase and is normally involved in the signal transduction pathways leading to cell growth and differentiation. Her-2/neu is thought to be an orphan receptor, with none of the EGF family of ligands able to activate it. However, ErbB receptors dimerize on ligand binding, and Her-2/neu is the preferential dimerization partner of other members of the ErbB family. The Her-2/neu gene is a proto-oncogene located at the long arm of human chromosome 17 (17q11.2-q12).

Approximately 25-30 percent of breast cancers, irrespective of whether they are estrogen positive or negative, have an amplification of the Her-2/neu gene or overexpression of its protein product. Overexpression and/or gene amplification of this receptor in breast cancer is associated with increased disease recurrence and worse prognosis.

In another preferred embodiment, it is provided that an additional mode of treatment for which prediction is sought is a treatment related to the signalling pathway of a receptor from the ErbB-family, the PDGFR-family and the C-KIT receptor.

Such treatment may include the administration of
an agonist of a ligand for receptors from the ErbB-family
an antagonist, e.g. an antibody or an antibody fragment, against said ligand and/or receptor,
an antisense nucleic acid inhibiting the expression of a gene encoding for said ligand and/or receptor,
a small molecular drug, and/or
a kinase inhibitor specific for the given receptor.

By way of illustration and not by way of restriction said agents may be selected from the group consisting of the agents shown in table 9.

TABLE 9

| Target | antagonist | Kinase inhibtors |
|---|---|---|
| Her-2/neu (ErbB-2) | Herceptin (Trastuzumab) Pertuzumab | Lapatinib (Tykerb) GW572016 AEE-788 CI-1033 |

TABLE 9-continued

| Target | antagonist | Kinase inhibtors |
|---|---|---|
| PDGFR | | Gleevec Nexavar Sutent |
| VEGFR | | Sutent Nexavar Axitinib Pazopanib |
| C-KIT receptor | | Gleevec Nexavar Sutent |

Other potential agents may be selected from the group comprising Cetuximab (tradename Erbitux®, target receptor is EGFR), Matuzumab (EMD7200, target receptor is EGFR), Trastuzumab (tradename Herceptin®, target receptor is Her-2/neu), Pertuzumab (target receptor is Her-2/neu), Bevacizumab (tradename Avastin®, target ligand is VEGFA), 2C3 (target ligand is VEGFA), VEGF-trap (AVE-0005, target ligands are VEGFA and PIGF), IMC-1121B (target receptor is VEGFR2), CDP-791 (target receptor is VEGFR2), Gefitinib (tradename Iressa®, ZD-1839, target receptor is EGFR), Erlotinib (tradename Tarceva®, OSI-774, target receptor is EGFR), EKB-569 (target receptor is EGFR), PKI-166 (target receptor is EGFR)), PKI-166 (target receptor is EGFR), Lapatinib (tradename Tycerb®, target receptor is EGFR and Her-2/neu), GW572016 (target receptors are EGFR and Her-2/neu), AEE-788 (target receptors are EGFR, Her-2/neu and VEGFR-2), CI-1033 (target receptors are EGFR, Her-2/neu and Her4), AZD6474 (target receptors are EGFR and VEGFR-2).

However, other treatments related to the ErbB receptor family signalling pathway which fall under the scope of the present invention comprise the administration of Sorafenib (tradename Nexavar®, BAY 43-9005, target receptors are VEGFR-2, VEGFR-3, c-KIT, PDGFR-B, RET and Raf-Kinase), BAY 57-9352 (target receptor is VEGFR-2), Sunitinib (tradename Sutent®, target receptors are VEGFR-1, VEGFR-2 and PDGFR), AG13925 (target receptors are VEGFR-1 and VEGFR-2), AG013736 (target receptors are VEGFR-1 and VEGFR-2), AZD2171 (target receptors are VEGFR-1 and VEGFR-2), ZD6474 (target receptors are VEGFR-1, VEGFR-2 and VEGFR-3), Vandetenib (ZD 7646), Vatalanib PTK-787/ZK-222584 (target receptors are VEGFR-1 and VEGFR-2), CEP-7055 (target receptors are VEGFR-1, VEGFR-2 and VEGFR-3), CP-547 (target receptors are VEGFR-1 and VEGFR-2), CP-632 (target receptors are VEGFR-1 and VEGFR-2), GW786024 (target receptors are VEGFR-1, VEGFR-2 and VEGFR-3), AMG706 (target receptors are VEGFR-1, VEGFR-2 and VEGFR-3), Imatinib mesylate (tradename Glivec®/Gleevec®, target receptors are bcr-abl and c-KIT), BMS-214662 (target enzyme is Ras farnesyl transferase), CCI-779 (target enzyme is mTOR), RAD0001 (tradename Everolismus®, target enzyme is mTOR), CI-1040 (target enzyme is MEK), SU6668 (target receptors are VEGFR-2, PDGFR-B and FGFR-1), AZD6126, CP547632 (target receptors are VEGFRs), CP868596 GW786034 (target receptors are PDGFRs), ABT-869 (target receptors are VEGFRs and PDGFRs), AEE788 (target receptors are VEGFRs and PDGFRs), AZD0530 (target enzymes are src and abl), and CEP7055.

In this context, other parameters may as well be used and combined in order to predict the therapeutic success for said given mode of treatment. The parameters may be chosen from the group consisting of
  Menopausal status
  Overall histological state
  ECOG performance status
  Serum Her-2/neu level
  Serum VEGFA level
  Serum EGFR level
  Serum MMP status
  Serum status of complement factors and its fragments (e.g. C3A)
  LDH serum levels In yet another preferred embodiment of the present invention, it is provided that said given mode of treatment (a) acts on recruitment of lymphatic vessels, angiogenesis, cell proliferation, cell survival and/or cell motility, and/or b) comprises administration of a chemotherapeutic agent.

Furthermore, it is provided in an another preferred embodiment of the present invention that said given mode of treatment comprises, in addition, administration of small molecule inhibitors, antibody based regimen, anti-proliferation regimen, pro-apoptotic regimen, pro-differentiation regimen, radiation and/or surgical therapy.

It is particularly preferred that, in the method according to the invention, the said expression level is determined by
  a) a hybridization based method,
  b) a PCR-based method, particularly a quantitative real-time PCR method,
  c) determining the protein level,
  d) a method based on the electrochemical detection of particular molecules,
  e) an array based method,
  f) serial analysis of gene expression (sage), and/or
  g) a Planar wave guide based method.

The above mentioned methods have in common that they are focused on the detection of nucleic acids, particularly on the detection of mRNA, DNA, PNA, LNA and/or Morpholino. Moreover, these methods provide the option to determine more than two agents at the same time ("multiplexing"). Therefore, not only the expression levels of one gene of interest can be determined, but the expression level of many other genes of interest, like other ligands, receptors, oncogenes or metabolism related genes can be determined in order to better characterize a given cancer or neoplastic disease in a patient.

In another preferred embodiment of the present invention it is provided that said cancer or neoplastic disease is characterized by a negative Estrogen receptor status, a negative progesterone receptor status and/or a negative Her-2/neu receptor status.

Among the different breast cancer subgroups, the group being characterized by negative statuses in all three aspects as mentioned above (also termed "basal tumors") has the worst prognosis.

A proper detection of this group is thus vital to sort out those patients which will draw any benefit from anti estrogen treatment, anti progesterone treatment and/or anti Her-2/neu treatment.

A different type of therapy, i.e. neodadjuvant chemotherapy, can thus be administered to these patients, in order to avoid side effects of the above mentioned treatments, and to improve therapy prediction.

Furthermore, in a preferred embodiment of the present invention it is provided that said cancer or neoplastic disease is selected from the group consisting of gynaecological cancers including Breast cancer, Ovarian cancer, Cervical cancer, Endometrial cancer, Vulval cancer, and the like.

In yet another preferred embodiment of the present invention it is provided that the expression level of at least one of the said gene/s is determined with RT-PCR (reverse transcriptase polymerase chain reaction) of the ligand and/or receptor related mRNA.

In another preferred embodiment of the present invention, it is provided that the expression level of at least one of the said gene/s is determined in formalin and/or paraffin fixed tissue samples.

In yet another preferred embodiment of the present invention, it is provided that the expression level of at least one of the said gene/s is determined in serum, plasma or whole blood samples.

Routinely, in tumor diagnosis tissue samples are taken as biopsies form a patient and undergo diagnostic procedures. For this purpose, the samples are fixed in formaline and/or parrafine and are then examined with immunohistochemistry methods. The formaline treatment leads to the inactivation of enzymes, as for example the ubiquitous RNA-digesting enzymes (RNAses). For this reason, the mRNA status of the tissue (the so called transcriptome), remains unaffected.

However, the formaline treatment leads to partial depolymerization of the individual mRNA molecules. For this reason, the current doctrine is that formaline fixed tissue samples can not be used for the analysis of the transcriptome of said tissue.

For this reason, it is provided in a preferred embodiment of the present invention that after lysis, the samples are treated with silica-coated magnetic particles and a chaotropic salt, in order to purify the nucleic acids contained in said sample for further determination.

Collaborators of the inventors of the present invention have developed an approach which however allows successful purification of mRNA out of tissue samples fixed in such manner, and which is disclosed, among others, in WO03058649, WO2006136314A1 and DE10201084A1, the content of which is incorporated herein by reference.

Said method comprises the use of magnetic particles coated with silica ($SiO_2$). The silica layer is closed and tight and is characterized by having an extremely small thickness on the scale of a few nanometers. These particles are produced by an improved method that leads to a product having a closed silica layer and thus entail a highly improved purity. The said method prevents an uncontrolled formation of aggregates and clusters of silicates on the magnetite surface whereby positively influencing the additional cited properties and biological applications. The said magnetic particles exhibit an optimized magnetization and suspension behavior as well as a very advantageous run-off behavior from plastic surfaces. These highly pure magnetic particles coated with silicon dioxide are used for isolating nucleic acids, including DNA and RNA, from cell and tissue samples, the separating out from a sample matrix ensuing by means of magnetic fields. These particles are particularly well-suited for the automatic purification of nucleic acids, mostly from biological body samples for the purpose of detecting them with different amplification methods.

The selective binding of these nucleic acids to the surface of said particles is due to the affinity of negatively charged nucleic acids to silica containing media in the presence of chaotropic salts like guanidinisothiocyanate. Said binding properties are known as the so called "boom principle". They are described in the European patent EP819696, the content of which is incorporated herein by reference.

The said approach is particularly useful for the purification of mRNA out of formaline and/or paraffin fixed tissue samples. In contrast to most other approaches, which leave very small fragments behind that are not suitable for later determination by PCR and/or hybridization technologies, the said approach creates mRNA fragments which are large enough to allow specific primer hybridzation and/or specific probe hybridization. A minimal size of at least 100 bp, more preferably 200 base pairs is needed for specific and robust detection of target gene expression. Moreover it is also necessary to not have too many inter-sample variations with regard to the size of the RNA fragments to guarantee comparability of gene expression results. Other issues of perturbance of expression data by sample preparation problems relate to the contamination level with DNA, which is lower compared to other bead based technologies. This of particular importance, as the inventors have observed, that DNAse treatment is not efficient in approximately 10% of FFPE samples generated by standard procedures and stored at room temperature for some years before cutting and RNA extraction.

The said approach thus allows a highly specific determination of candidate gene expression levels with one of the above introduced methods, particularly with hybridization based methods, PCR based methods and/or array based methods, even in formaline and/or paraffine fixed tissue samples, and is thus extremely beneficial in the context of the present invention, as it allows the use of tissue samples fixed with formaline and/or paraffine, which are available in tissue banks and connected to clinical databases of sufficient follow-up to allow retrospective analysis.

Furthermore, a kit useful for carrying out one of the said methods is provided, said kit comprising at least
 a) a primer pair and/or a probe each having a sequence sufficiently complementary to at least one gene according to the invention, and/or
 b) an antibody directed against an expression product related to at least one gene according to the invention.

In yet another embodiment of the invention a a method for correlating the clinical outcome of a patient suffering from or at risk of developing a neoplastic disease is provided, said method comprising the steps of:
 a) obtaining a fixed biological sample from said patient;
 b) determining the expression level of at least one gene of interest in said sample according to any of the above methods, and
 c) correlating the pattern of expression levels determined in (b) with said patient's data, said data being selected from the group consisting of etiopathology data, clinical symptoms, anamnesis data and/or data concerning the therapeutic regimen.

The said method is particularly beneficial for epidemiological studies. These studies profit from the fact that large tissue databases exist comprising paraffin and/or formalin fixed tissue samples together with an extensive documentation of the patient's history, including etiopathology data, clinical symptoms, anamnesis data and/or data concerning the therapeutic regimen.

The said methods allows for large scale studies which comprise the correlation of the clinical outcome of a patient suffering from or at risk of developing a neoplastic disease with a negative or a positive Estrogen receptor status. In order to successfully adopt this approach, the above introduced method for mRNA purification comprising silica coated magnetic beads and chaotropic salts is quite helpful.

Furthermore, the present invention provides a nucleic acid molecule, selected from the group consisting of
 a) the nucleic acid molecule presented as SEQ ID NO:1-28;
 b) a nucleic acid molecule having a length of 4-80 nucleotides, preferably 18-30 nucleotides, the sequence of which corresponds to the sequence of a single stranded fragment of a gene encoding for a ligand and/or receptor selected from the group consisting of ESR1, ESR2, PGR, EGFR, Her-2/neu, ERBB3, ERBB4, MLPH, MMP1, MMP7, MMP9, MMP11, MMP10, MMP13 and immune genes such as IGHM IGHG, IGHD, IGLC, IGLJ, IGLL, IGLV;
 c) a nucleic acid molecule that is a fraction, variant, homologue, derivative, or fragment of the nucleic acid molecule presented as SEQ ID NO: 1-28;
 d) a nucleic acid molecule that is capable of hybridizing to any of the nucleic acid molecules of a)-c) under stringent conditions;
 e) a nucleic acid molecule that is capable of hybridizing to the complement of any of the nucleic acid molecules of a)-d) under stringent conditions;
 f) a nucleic acid molecule that is capable of hybridizing to the complement of a nucleic acid molecule of e);
 g) a nucleic acid molecule having a sequence identity of at least 95% with any of the nucleic acid molecules of a)-f);
 h) a nucleic acid molecule having a sequence identity of at least 70% with any of the nucleic acid molecules of a)-f);
 i) a complement of any of the nucleic acid molecules of a)-h), or
 j) a nucleic acid molecule that comprises any nucleic acid molecule of a)-i).

See table 12 for a sequence listing. These nucleic acids are being used either as primers for a polymerase chain reaction protocol, or as detectable probes for monitoring the said process.

Furthermore it is provided that the said nucleic acid is selected from the group consisting of DNA, RNA, PNA, LNA and/or Morpholino. The nucleic acid may, in a preferred embodiment, be labelled with at least one detectable marker. This feature is applicable particularly for those nucleic acids which serve as detectable probes for monitoring the polymerase chain reaction process Such detectable markers may for example comprise at least one label selected from the group consisting of fluorescent molecules, luminescent molecules, radioactive molecules, enzymatic molecules and/or quenching molecules.

In a particularly preferred embodiment, the said detectable probes are labeled with a fluorescent marker at one end and a quencher of fluorescence at the opposite end of the probe. The close proximity of the reporter to the quencher prevents detection of its fluorescence; breakdown of the probe by the 5' to 3' exonuclease activity of the taq polymerase breaks the reporter-quencher proximity and thus allows unquenched emission of fluorescence, which can be detected. An increase in the product targeted by the reporter probe at each PCR cycle therefore causes a proportional increase in fluorescence due to the breakdown of the probe and release of the reporter.

In another preferred embodiment of the present invention, a kit of primers and/or detection probes is provided, comprising at least one of the nucleic acids according to the above enumeration and/or their fractions, variants, homologues, derivatives, fragments, complements, hybridizing counterparts, or molecules sharing a sequence identity of at least 70%, preferably 95%.

Said kit may, in another preferred embodiment, comprise at least one of the nucleic acid molecules presented as SEQ ID NO: 1-28, and/or their fractions, variants, homologues, derivatives, fragments, complements, hybridizing counterparts, or molecules sharing a sequence identity of at least 70%, preferably 95%, for the detection of at least one gene of interest.

Furthermore, the use of a nucleic acid according as recited above, or of a kit as recited above for the prediction of a clinical response of a patient suffering from or at risk of developing a neoplastic disease towards a given mode of treatment.

Disclaimer

To provide a comprehensive disclosure without unduly lengthening the specification, the applicant hereby incorporates by reference each of the patents and patent applications referenced above.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

BRIEF DESCRIPTION OF THE EXAMPLES AND DRAWINGS

Additional details, features, characteristics and advantages of the object of the invention are disclosed in the subclaims, and the following description of the respective figures and examples, which, in an exemplary fashion, show preferred embodiments of the present invention. However, these drawings should by no means be understood as to limit the scope of the invention.

Example 1

Core needle biopsy specimen of breast tumors, which had been formalin fixed (FFPE tissues) or were available as fresh tissues were analyzed. Formalin fixed tissues were available from breast cancer patients (≥cT2, N0/N1, M0) receiving neoadjuvant chemotherapy of 4 cycles of epirubicin and cyclophosphamide (90/600 mg/m$^2$) followed by 4 cycles paclitaxel (175 mg/m$^2$). Trastuzumab was administered parallel to paclitaxel therapy on a three weekly dose (6 mg/kg) and continued for 33 weeks after surgery (according to the TECHNO trial) if tumors were IHC positive (e.g DAKO status 3 with intense and continuous membrane staining) or FISH positive (e.g. >2.1 gene copies of Her-2/neu gene per nucleus). Patients with Her-2/neu negative tumors (equally to IHCl+ or FISH negative testing) were not treated with trastuzumab (PREPARE trial). The Her-2/neu status was determined in core-needle biopsies of all patients by immunohistochemistry or FISH analysis at a central reference pathology department. In total 853 Paraffin embedded core needle biopsies were used for analysis. In addition, 86 fresh tissue specimen were used from breast cancer patients ((≥cT1-4, N0/N1, M0) receiving neoadjuvant chemotherapy of 4 to 6 cycles of epirubicin and cydophosphamide (90/600 mg/m$^2$) 14 days apart. The samples were flash-frozen and analyzed by microarrays.

Analysis of MMP genes (in particular MMP7), MLPH, Keratins (in particular Keratin 5) and genes related to the Immune System such as the immunoglobulin gene family (e.g. IGHM, IGHG, IGHD, IGLC, IGLJ, IGLL, IGLV and the like were informative and did predict response to neoadjuvant chemotherapy.

Combinatorial analysis of genes such as MMP7, Keratin 5, MLPH and IGHM status on the RNA level were possible and meaningful in fresh tissue specimen by commercially available Affymetrix GeneArrays and in FFPE tissues from core needle biopsies despite highly variable tumor contents. Overall there was a good correlation between the different IHC, FISH and qPGR methods for standard markers such as ESR1 and Her-2/neu, although the tumor cell content of the tissues varied substantially with 46% of the tumors having a tumor cell content of >50% and 16% of the tumors having less than 20% tumor cells (median 40%).

Example 2

The determination of high MMP7 and low MLPH and Her-2/neu expression levels identified a population of breast tumors having a particularly good response to chemotherapy. By this combined analysis we could identify a subpopulation of ESR1 negative tumors that drew benefit from neoadjuvant treatment consisting of an anthracyclin and cyclophosphamid and therefore could be spared from additional regimen (such as Taxol).

Example 3

A group of patients was treated with adjuvant anthracycline-based dose-dense sequential chemotherapy (E-CMF vs. E-T-CMF) in the context of a randomized Phase III study. RNA was isolated from 217 fixed tumor tissue samples employing an experimental method based on magnetic beads from Siemens Medical Solutions Diagnostics, followed by kinetic one-step RT-PCR for mRNA expression analysis. Identification of molecular subtypes was based on 2D hierarchical clustering of four genes. One of these genes (melanophilin, MLPH) is known to be associated with ESR1-positive tumors only.

Figure 2:
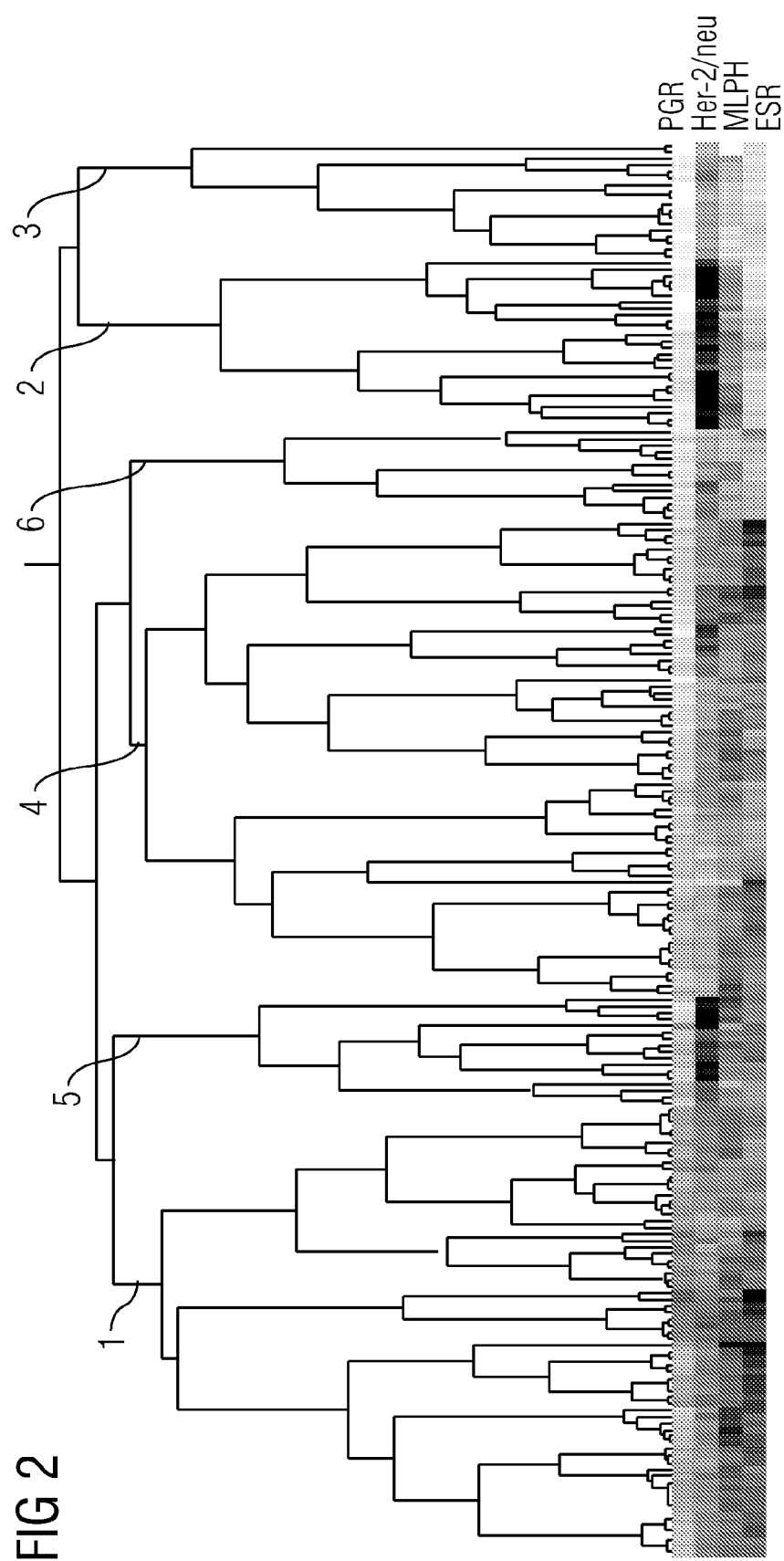
FIG. 2 shows identification of the basal-like subtypes based on 2D hierarchical clustering.

The hierarchical clustering based on ESR, PGR, Her-2/neu, and MLPH mRNA expression resulted into 6 identifiable groups, i.e.
1=ESR and PGR positive
5=ESR and Her-2/neu positive
4=ESR less positive and PGR negative
6=Basal Like with some ESR and Her-2/neu activity left
2=Her-2/neu positive and ESR negative
3=Basal like with lowest ESR and PGR activity See FIG. 2 for an illustration. Furthermore, two groups (groups 6 and 3) of low (basal-like, 14+18=32 of 217, 15%) and two groups (1 and 5) of high (86 of 217, 40%) mRNA expression were identified.

Patients with basal-like tumors (i.e. groups 6 and 3) were found to have significantly shorter overall survival (p=0.02) compared to the patients with high mRNA expression. No difference was found in terms of disease-free survival (p=0.373) (see FIGS. 3 and 4). Interestingly, survival of basal-like patients appears to reach a plateau after the 5th year, with neither recurrences nor deaths being observed during an additional 4 years of follow-up.

The results of this study confirm that basal-like patients, identified by only four genes among high-risk breast cancer patients, have a poor prognosis. Confirmation studies are currently being performed by evaluating specific basal-like genes.

It is worth mentioning that the above analysis has been carried out
- on the basis of the determination of the expression level of four genes only (alternatively, genes can be determined which are coexpressed with any of these genes), and
- on the basis of Formalin-Fixed Paraffin-Embedded Tissue.

Methods according to the state of the art (as disclosed in Sorlie et al., 2001) require the analysis of more than 500 genes, and the use of fresh tissue. While the first advantage is due to intelligent test design, the later is due to use of the Siemens Proprietary magnetic bead technology (see claim XX and discussion).

Example 4

In order to investigate possible differential EGF and VEGF receptor mRNA expression in the two basal-like subtypes described in Example 3, the following experiment was carried out.

Patients were treated with adjuvant anthracycline-based dose-dense sequential chemotherapy (E-CMF vs. E-T-CMF) in the context of a randomized Phase III study. RNA was isolated from 217 fixed tumor tissue samples, followed by kinetic one-step RT-PCR for mRNA expression analysis of EGFR, VEGFR2 and VEGFR3. Identification of the basal-like subtypes was based on 2D hierarchical clustering.

One of the basal-like subtypes (14 of 217 patients, 6%, group 6 of Example 3) was found to retain some expression of the Her-2/neu, ESR and MLPH genes.

The second basal-like subtype (18 of 217 patients, 8%, group 3 of Example 3) was characterized by low mRNA expression of all four genes. Significantly more patients in group 6 exhibited high VEGFR2 and VEGFR3 mRNA expression compared to group 3 (Fisher's exact test, $p=0.026$ and $p=0.025$, respectively).

Patients being thus characterised might therefore receive benefit from anti VEGF-therapy, for example with sunitinib (Sutent), sorafenib (Nexavar), axitinib, and pazopanib.

In contrast, no such difference was observed for EGFR mRNA expression, i.e. both groups featured a relatively high EGFR gene expression. This means that significantly more patients in the two basal-like subtypes exhibited high EGFR mRNA expression compared to a group of non-basal-like patients (86 of 217, 40%) exhibiting high mRNA expression of all four genes ($p<0.0001$).

The results of this retrospective study suggest that patients from both basal-like subtypes may be candidates for new anti-EGFR agents. However, agents targeting the VEGF receptor family may only be active in the subgroup of basal-like patients retaining some expression of the Her-2, ESR and MLPH genes (group 6).

Example 5

Further analysis revealed that in tumors of group 3 the gene Birc5 (survivin) is highly expressed (no data shown). This gene has the following specification

TABLE 10

Survivin gene

| Gene Symbol | MapLocation | LocusLink | OMIM | UniGene | RefSeq Transcript |
|---|---|---|---|---|---|
| BIRC5 | chr17q25 | | 603352 | Hs.514527 | |

Survivin is a member of inhibitors of apoptosis (IAPs) family, which are upregulated in various malignancies. It has been described that high survivin expression is associated with favorable outcome of some carcinomas after radiation therapy (Freier et al. (2007).

This means that group 3 tumors, while not likely to be affected by anti VEGF therapy, might be susceptible to radiation therapy.

It is worth to be mentioned that a differentiation of the two basal-like subtypes (i.e. groups 3 and 6) has for the first time been described here.

So far, basal-like subtype tumors were classified as high-risk breast cancer patients, associated with poor prognosis. The differentiation as described above opens new ways to provide a more specific therapy to the patients affected, i.e. anti VEGF therapy (for group 6) or radiotherapy (for group 3). This has so far not been possible.

FIG. 1

The inventors have further analyzed said genes in breast carcinomas treated with neoadjuvant chemotherapeutic treatments (e.g. EC, EC-T, TAC) to analyze whether these tumors do respond to chemotherapeutic regimen. These analysis were done by Affymetrix array analysis (HG U133A) in fresh tissue biopsies or RT-kPCR analysis in fixed tissue biopsies of high risk breast tumors. It was found that >60% of these tumors do respond to chemotherapeutic regimen by pathological complete response, meaning no tumor is left after chemotherapeutic regimen in the primary tumor site or in the lymphnodes. This reflects a more that 4 fold higher response rate in this subgroup of patients compared to the unstratified cohort which reflected an approximately 15% pCR rate. 50% of all pathological complete responding breast tumors were within this subgroup of patients, which reflected approximately 15% of all patients. Breast tumors exhibiting a pathological complete response after chemotherapeutic treatment exhibit a good prognosis.

In addition, if tumors were further selected on basis of high immune marker expression, such as IGHM expression levels, approximately 90% of the tumors having high MMP7 and low MLPH level exhibited pathological complete response as depicted in FIG. 2.

Hormonal receptor status and Her-2/neu over-expression are important prognostic variables in patients with operable breast cancer. The majority of basal-like tumors are triple-negative for estrogen receptors (ESR), progesterone (PGR) and Her-2/neu receptors. Such tumors are found in approximately 12% of breast cancer patients and have been shown to have a poor prognosis.

FIG. 2

FIG. 2 shows identification of the basal-like subtypes based on 2D hierarchical clustering, as described in Example 3. Green indicates low gene expression, whereas red indicates high gene expression The Molecular classification was based on only four genes (estrogen receptors (ESR), progesterone receptors (PGR), Her-2/neu, and melanophilin (MLPH).

The analysis revealed the following tumor types:
1=ESR and PGR positive
5=ESR and Her-2/neu positive
4=ESR less positive and PGR negative
6=Basal Like with some ESR and Her-2/neu activity left
2=Her-2/neu positive and ESR negative
3=Basal like with lowest ESR and PGR activity The following table gives an overview about the different groups and potential therapeutic approaches:

TABLE 11a tumor groups classifiable with the method according to the invention, and possible therapies

| group | Marker status/ expression level | Tumor status | Therapy approach |
|---|---|---|---|
| 1 | ESR and PGR positive | ESR positive | Endocrine therapy, i.e. tamoxifen |
| 5 | ESR and Her-2/neu positive, PGR on a medium level | ESR positive | Endocrine therapy in combination with anti-ErbB therapy (i.e. trastuzumab) |
| 4 | ESR on a medium level, PGR negative, Her-2/neu | | |
| 6 | some residual ESR and Her-2/neu activity left, PGR negative | "triple negative", Basal like Tumor | anti VEGF therapy (i.e. Nexavar); optionally: new anti-ErbB therapy |
| 2 | Her-2/neu positive and ESR negative | | anti ErbB therapy (i.e. trastuzumab) |
| 3 | ESR and PGR almost zero, some residual Her-2/neu activity left | "triple negative", Basal like Tumor Birc5 (survivin) high | anti VEGF therapy (i.e. Nexavar); optionally: new anti-ErbB therapy. Radiotherapy due to coexpression of Birc5 |

Furthermore, as mentioned above, groups 3 and 6 can be further specified with respect to their CCND, BRCA1 and RB1 status, namely by means of detecting the MMP7 and/or MLPH status. This in turn may open up complementary therapeutic approaches:

TABLE 11b tumor groups classifiable with another method according to the invention, and possible therapies

| group | Marker status/ expression level | Tumor status | Therapy approach |
|---|---|---|---|
| 3 or 6 | MMP7 positive and/or MLPH positive | CCND negative RB1 negative BRCA1 negative | inhibition of homologous reconbination repairm (e.g. PARP1 inhbition) |

Figure 3:
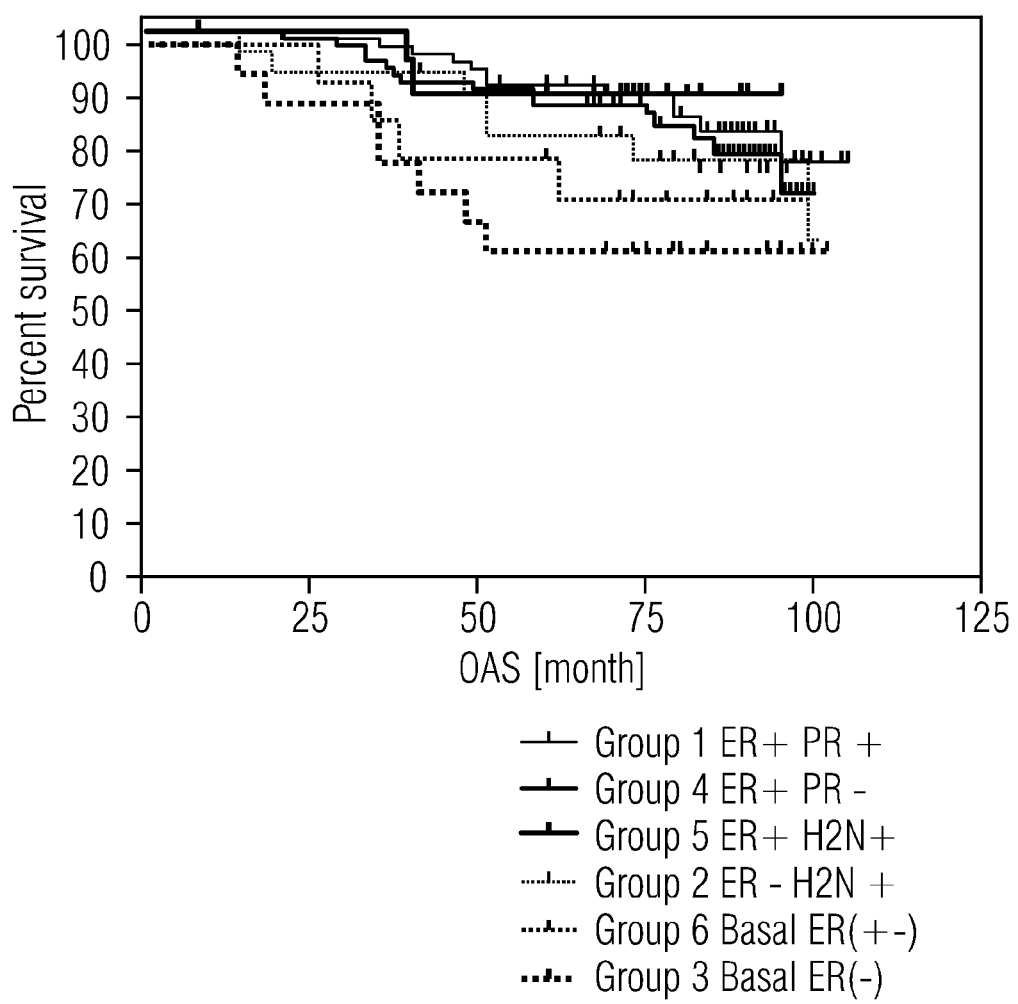
FIGS. 3 and 4 show Kaplan Meyer curves in which, for the different groups determined as above (see Example 3), the overall survival time (OAS) is plotted versus the respectie percentage.
Figure 4:
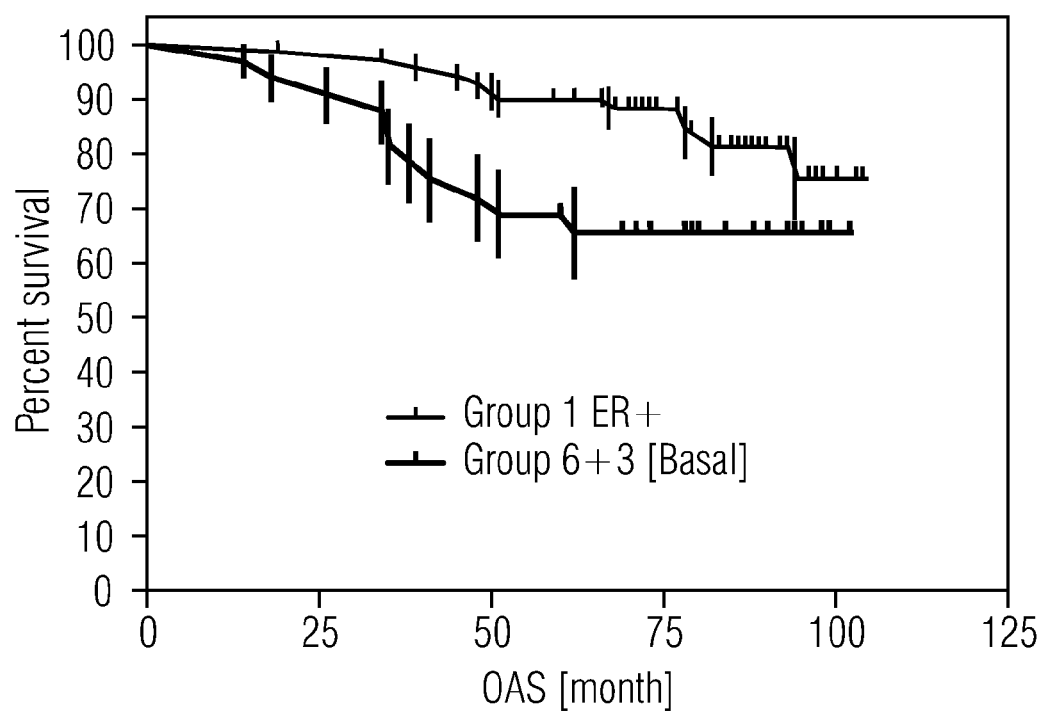

FIGS. 3 and 4

FIGS. 3 and 4 show Kaplan Meyer curves in which, for the different groups determined as above (see Example 3), the overall survival time (OAS) is plotted versus the respective percentage. It is obvious that the basal-like subtypes (groups 6 and 3) have the worst survival rates, and are thus associated with poor prognosis. For this reason, it is vital that the method according to the invention provides a method to detect these subtypes, in order to submit the respective patients to different and/or novel treatments.

APPENDIX

Primer Sequences

TABLE 12 primer sequences and probe sequences used in accordance with the present invention

| SEQ ID | Gene | PCR probe | Forward primer | Reverse primer |
|---|---|---|---|---|
| 1-3 | ERBB2 Her-2/neu | AGGCCAAGTCC GCAGAAGCCCT | TCTGGACGTG CCAGTGTGAA | CCTGCTCCCT GAGGACACAT |
| 4-6 | ERBB2 Her-2/neu | ACCAGGACCCA CCAGAGCGGG | CCAGCCTTCGA CAACCTCTATT | TGCCGTAGGT GTCCCTTTG |
| 7-9 | ERBB2 Her-2/neu | TGATCATGGTCAAATG TTGGATGATTGACTC | CCATCTGCACCA TTGATGTCTAC | CGGAATCTTG GCCGACATT |
| 9-12 | ERBB2 Her-2/neu | AAGATTCCCCT TCTTCCTGGGA | ACGCCCTCAG AAGATTGGAA | TGTGCTGACGC AAGCTACAAC |
| 13-15 | MLPH | CCAGCAGGCAGA GAGCGAGGTTTC | GCAGTGACGG CCTCAGAAG | CTGCAATCCTG GATTCAATGTC |
| 16-18 | MLPH | CCAAATGCAGACC CTTCAAGTGAGGC | TCGAGTGGCT GGGAAACTTG | AGATAGGGCA CAGCCATTGC |
| 19-21 | MLPH | CGGGCGTCTTCTGA GAGTCAGATCTTTG | CGATGTGGACA CCTCTGATGA | AGGCATTCCACA GCTGAAATATG |

TABLE 12-continued primer sequences and probe sequences used in accordance with the present invention

| SEQ ID | Gene | PCR probe | Forward primer | Reverse primer |
|---|---|---|---|---|
| 22-24 | MMP7 | CAGTCTAGGGATTA ACTTCCTGTATGCT | GAACGCTGGA CGGATGGTA | GAATGGCCAAG TTCATGAGTTG |
| 25-28 | MMP7 | AGTGGGAACAGGCTCA GGACTATCTCAAGAG | CGGGAGGCAT GAGTGAGCTA | GGCATTTTTGTT TCTGAGTCATAGA |

LIST OF REFERENCES

Freier et al., *Int. J. Cancer* Volume 120, Issue 4, Pages 942-946 (2007)
Faneyte et al., British Journal of Cancer 88, 406-412 (2003)
Ring et al., Endocr Relat Cancer 11: 643-658 (2004)
Sorlie et al., PNAS 98(19): 10869-74 (2001)

What is claimed is:

1. A method of analyzing a breast cancer sample taken from a patient which method comprises the use of three different nucleic acid molecules each labelled with one or more molecules selected from the group consisting of fluorescent molecules, luminescent molecules, radioactive molecules, enzymatic molecules and/or quenching molecules, wherein the three different labelled nucleic acid molecules having a length of 4-80 nucleotides and are capable of hybridizing under stringent conditions to the three different genes selected from the group consisting of ESR1, ESR2, PGR, and Her-2/neu;

wherein said method comprises the step of:

(i) contacting the three different labelled nucleic acid molecules with a breast cancer sample obtained from a patient, (ii) after contacting the sample with the three different labeled nucleic acid molecules, measuring the expression levels of the three different genes in the breast cancer sample by means of a polymerase chain reaction-based method, and (iii) characterising the type of the breast cancer sample according to the outcome of step (ii);

wherein the polymerase chain reaction-based method comprises the use of a recombinant Taq Polymerase;

wherein the method further comprises (v) a step of treating the patient with at least one of d) in case of positive Her-2/neu expression, anti-ErbB therapy, selected from the group consisting of anti ErbB2 antibodies, and ErbB2 kinase inhibitors;

e) in case of a low or negative expression of ESR, PGR, and Her-2/neu, chemotherapy and/or anti VEGF therapy selected from the group consisting of anti VEGF antibodies, anti-VEGF Fc-Receptor fusion peptides, and VEGFR kinase inhibitors, and/or f) in case of positive expression of ESR and PGR, endocrine therapy, wherein the endocrine therapy comprises the administration of an estrogen receptor antagonist selected from the group consisting of Tamoxifen, Raloxifene, Faslodex, Anastrozole, Exemestane Letrozole and Megestrol acetate.

2. The method according to claim 1, characterized in that the said three different labelled nucleic acid molecules are selected from the group consisting of DNA, RNA, PNA, LNA, and Morpholino.

3. The method according to claim 1, wherein the three different labelled nucleic acid molecules are labeled with at least one detectable marker.

4. The method according to claim 1, further comprising at least three nucleic acids selected from each group (i), (ii), and (iii), wherein (i), (ii), and (iii) consists of: (i) IGHM, IGHG, IGHD, IGLC, IGLJ, IGLL, IGLV, or CXCL9, (ii) Birc5, STC3, and/or Top2A, and CXCL9, (iii) VEGFR, PDGFR, Her2/neu and C-KIT.

* * * * *

SEQUENCE LISTING

<160> NUMBER OF SEQ ID NOS: 27

<210> SEQ ID NO 1
<211> LENGTH: 22
<212> TYPE: DNA
<213> ORGANISM: Artificial
<220> FEATURE:
<223> OTHER INFORMATION: ERBB2  Her-2/neu

<400> SEQUENCE: 1
aggccaagtc cgcagaagcc ct                                      22

<210> SEQ ID NO 2
<211> LENGTH: 20
<212> TYPE: DNA
<213> ORGANISM: Artificial
<220> FEATURE:
<223> OTHER INFORMATION: ERBB2  Her-2/neu

<400> SEQUENCE: 2
tctggacgtg ccagtgtgaa                                         20

<210> SEQ ID NO 3
<211> LENGTH: 20
<212> TYPE: DNA
<213> ORGANISM: Artificial
<220> FEATURE:
<223> OTHER INFORMATION: ERBB2  Her-2/neu

<400> SEQUENCE: 3
cctgctccct gaggacacat                                         20

<210> SEQ ID NO 4
<211> LENGTH: 21
<212> TYPE: DNA
<213> ORGANISM: Artificial
<220> FEATURE:
<223> OTHER INFORMATION: ERBB2  Her-2/neu

<400> SEQUENCE: 4
accaggaccc accagagcgg g                                       21

<210> SEQ ID NO 5
<211> LENGTH: 22
<212> TYPE: DNA

```
<213> ORGANISM: Artificial
<220> FEATURE:
<223> OTHER INFORMATION: ERBB2  Her-2/neu

<400> SEQUENCE: 5
ccagccttcg acaacctcta tt                                              22

<210> SEQ ID NO 6
<211> LENGTH: 19
<212> TYPE: DNA
<213> ORGANISM: Artificial
<220> FEATURE:
<223> OTHER INFORMATION: ERBB2  Her-2/neu

<400> SEQUENCE: 6
tgccgtaggt gtccctttg                                                  19

<210> SEQ ID NO 7
<211> LENGTH: 31
<212> TYPE: DNA
<213> ORGANISM: Artificial
<220> FEATURE:
<223> OTHER INFORMATION: ERBB2  Her-2/neu

<400> SEQUENCE: 7
tgatcatggt caaatgttgg atgattgact c                                    31

<210> SEQ ID NO 8
<211> LENGTH: 23
<212> TYPE: DNA
<213> ORGANISM: Artificial
<220> FEATURE:
<223> OTHER INFORMATION: ERBB2  Her-2/neu

<400> SEQUENCE: 8
ccatctgcac cattgatgtc tac                                             23

<210> SEQ ID NO 9
<211> LENGTH: 19
<212> TYPE: DNA
<213> ORGANISM: Artificial
<220> FEATURE:
<223> OTHER INFORMATION: ERBB2  Her-2/neu

<400> SEQUENCE: 9
cggaatcttg gccgacatt                                                  19

<210> SEQ ID NO 10
<211> LENGTH: 22
<212> TYPE: DNA
<213> ORGANISM: Artificial
<220> FEATURE:
<223> OTHER INFORMATION: ERBB2  Her-2/neu

<400> SEQUENCE: 10
aagattcccc ttcttcctgg ga                                              22

<210> SEQ ID NO 11
<211> LENGTH: 20
<212> TYPE: DNA
<213> ORGANISM: Artificial
<220> FEATURE:
<223> OTHER INFORMATION: ERBB2  Her-2/neu

<400> SEQUENCE: 11
acgccctcag aagattggaa                                                 20
```

<210> SEQ ID NO 12
<211> LENGTH: 21
<212> TYPE: DNA
<213> ORGANISM: Artificial
<220> FEATURE:
<223> OTHER INFORMATION: ERBB2 Her-2/neu

<400> SEQUENCE: 12
tgtgctgacg caagctacaa c                                              21

<210> SEQ ID NO 13
<211> LENGTH: 24
<212> TYPE: DNA
<213> ORGANISM: Artificial
<220> FEATURE:
<223> OTHER INFORMATION: MLPH

<400> SEQUENCE: 13
ccagcaggca gagagcgagg tttc                                           24

<210> SEQ ID NO 14
<211> LENGTH: 19
<212> TYPE: DNA
<213> ORGANISM: Artificial
<220> FEATURE:
<223> OTHER INFORMATION: MLPH

<400> SEQUENCE: 14
gcagtgacgg cctcagaag                                                 19

<210> SEQ ID NO 15
<211> LENGTH: 22
<212> TYPE: DNA
<213> ORGANISM: Artificial
<220> FEATURE:
<223> OTHER INFORMATION: MLPH

<400> SEQUENCE: 15
ctgcaatcct ggattcaatg tc                                             22

<210> SEQ ID NO 16
<211> LENGTH: 26
<212> TYPE: DNA
<213> ORGANISM: Artificial
<220> FEATURE:
<223> OTHER INFORMATION: MLPH

<400> SEQUENCE: 16
ccaaatgcag acccttcaag tgaggc                                         26

<210> SEQ ID NO 17
<211> LENGTH: 20
<212> TYPE: DNA
<213> ORGANISM: Artificial
<220> FEATURE:
<223> OTHER INFORMATION: MLPH

<400> SEQUENCE: 17
tcgagtggct gggaaacttg                                                20

<210> SEQ ID NO 18
<211> LENGTH: 20
<212> TYPE: DNA
<213> ORGANISM: Artificial
<220> FEATURE:

<223> OTHER INFORMATION: MLPH

<400> SEQUENCE: 18
agatagggca cagccattgc                    20

<210> SEQ ID NO 19
<211> LENGTH: 28
<212> TYPE: DNA
<213> ORGANISM: Artificial
<220> FEATURE:
<223> OTHER INFORMATION: MLPH

<400> SEQUENCE: 19
cgggcgtctt ctgagagtca gatctttg            28

<210> SEQ ID NO 20
<211> LENGTH: 21
<212> TYPE: DNA
<213> ORGANISM: Artificial
<220> FEATURE:
<223> OTHER INFORMATION: MLPH

<400> SEQUENCE: 20
cgatgtggac acctctgatg a                   21

<210> SEQ ID NO 21
<211> LENGTH: 23
<212> TYPE: DNA
<213> ORGANISM: Artificial
<220> FEATURE:
<223> OTHER INFORMATION: MLPH

<400> SEQUENCE: 21
aggcattcca cagctgaaat atg                 23

<210> SEQ ID NO 22
<211> LENGTH: 28
<212> TYPE: DNA
<213> ORGANISM: Artificial
<220> FEATURE:
<223> OTHER INFORMATION: MMP7

<400> SEQUENCE: 22
cagtctaggg attaacttcc tgtatgct            28

<210> SEQ ID NO 23
<211> LENGTH: 19
<212> TYPE: DNA
<213> ORGANISM: Artificial
<220> FEATURE:
<223> OTHER INFORMATION: MMP7

<400> SEQUENCE: 23
gaacgctgga cggatggta                      19

<210> SEQ ID NO 24
<211> LENGTH: 22
<212> TYPE: DNA
<213> ORGANISM: Artificial
<220> FEATURE:
<223> OTHER INFORMATION: MMP7

<400> SEQUENCE: 24
gaatggccaa gttcatgagt tg                  22

```
<210> SEQ ID NO 25
<211> LENGTH: 31
<212> TYPE: DNA
<213> ORGANISM: Artificial
<220> FEATURE:
<223> OTHER INFORMATION: MMP7

<400> SEQUENCE: 25
agtgggaaca ggctcaggac tatctcaaga g                              31

<210> SEQ ID NO 26
<211> LENGTH: 20
<212> TYPE: DNA
<213> ORGANISM: Artificial
<220> FEATURE:
<223> OTHER INFORMATION: MMP7

<400> SEQUENCE: 26
cgggaggcat gagtgagcta                                           20

<210> SEQ ID NO 27
<211> LENGTH: 26
<212> TYPE: DNA
<213> ORGANISM: Artificial
<220> FEATURE:
<223> OTHER INFORMATION: MMP7

<400> SEQUENCE: 27
ggcatttttt gtttctgagt cataga                                    26
```